US012430729B2

(12) United States Patent
Asanuma et al.

(10) Patent No.: US 12,430,729 B2
(45) Date of Patent: Sep. 30, 2025

(54) OPHTHALMIC APPARATUS, METHOD OF CONTROLLING THE SAME, AND RECORDING MEDIUM

(71) Applicant: Topcon Corporation, Tokyo (JP)

(72) Inventors: Kazunori Asanuma, Tokyo (JP); Yusuke Ono, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 709 days.

(21) Appl. No.: 17/780,038

(22) PCT Filed: Dec. 21, 2020

(86) PCT No.: PCT/JP2020/047607
§ 371 (c)(1),
(2) Date: May 26, 2022

(87) PCT Pub. No.: WO2021/153086
PCT Pub. Date: Aug. 5, 2021

(65) Prior Publication Data
US 2022/0414845 A1  Dec. 29, 2022

(30) Foreign Application Priority Data
Jan. 30, 2020 (JP) ................... 2020-013119

(51) Int. Cl.
*A61B 3/107* (2006.01)
*A61B 3/00* (2006.01)
(Continued)

(52) U.S. Cl.
CPC .............. *G06T 5/80* (2024.01); *A61B 3/0025* (2013.01); *A61B 3/102* (2013.01); *A61B 3/107* (2013.01);
(Continued)

(58) Field of Classification Search
CPC .... G06T 5/80; G06T 7/13; G06T 7/50; G06T 2207/10101; G06T 2207/30041;
(Continued)

(56) References Cited

U.S. PATENT DOCUMENTS

2009/0149742 A1  6/2009 Kato et al.
2012/0140174 A1  6/2012 Hee et al.
(Continued)

FOREIGN PATENT DOCUMENTS

EP     4 098 174 A1    12/2022
JP     2009-142313 A    7/2009
(Continued)

OTHER PUBLICATIONS

Office Action issued Jul. 30, 2024 in Japanese Patent Application No. 2020-013119 with machine English translation thereof.
(Continued)

*Primary Examiner* — Tuyen Tra
(74) *Attorney, Agent, or Firm* — XSENSUS LLP

(57) ABSTRACT

An ophthalmic apparatus of an aspect example includes an image acquiring unit, a corneal shape estimating processor, and a first image correcting processor. The image acquiring unit is configured to acquire an anterior segment image constructed based on data collected from an anterior segment of a subject's eye by optical coherence tomography (OCT) scanning. The anterior segment image includes a missing part corresponding to a part of a cornea. The corneal shape estimating processor is configured to estimate a shape of the missing part of a cornea image by analyzing the anterior segment image acquired by the image acquiring unit. The first image correcting processor is configured to correct distortion of the anterior segment image based at least on the shape of the missing part estimated by the corneal shape estimating processor.

14 Claims, 16 Drawing Sheets

(51) Int. Cl.
  *A61B 3/10* (2006.01)
  *A61B 3/117* (2006.01)
  *A61B 3/14* (2006.01)
  *G06T 5/80* (2024.01)
  *G06T 7/13* (2017.01)
  *G06T 7/50* (2017.01)

(52) U.S. Cl.
  CPC ............... *A61B 3/117* (2013.01); *A61B 3/14* (2013.01); *G06T 7/13* (2017.01); *G06T 7/50* (2017.01); *G06T 2207/10101* (2013.01); *G06T 2207/30041* (2013.01)

(58) Field of Classification Search
  CPC ......... G06T 5/77; A61B 3/0025; A61B 3/102; A61B 3/107; A61B 3/117; A61B 3/14
  See application file for complete search history.

(56) References Cited

U.S. PATENT DOCUMENTS

| | | |
|---|---|---|
| 2012/0271288 A1 | 10/2012 | Marziliano et al. |
| 2013/0107209 A1 | 5/2013 | Hacker et al. |
| 2013/0188140 A1 | 7/2013 | Bagherinia et al. |
| 2013/0208240 A1 | 8/2013 | Sharma et al. |
| 2013/0242259 A1 | 9/2013 | Hacker et al. |
| 2013/0258280 A1 | 10/2013 | Goto |
| 2013/0301008 A1 | 11/2013 | Srivastava et al. |
| 2015/0085252 A1 | 3/2015 | Fujimura et al. |
| 2015/0245765 A1 | 9/2015 | Fujii et al. |
| 2016/0317012 A1 | 11/2016 | Bagherinia |
| 2016/0317029 A1 | 11/2016 | Srivastava et al. |
| 2016/0345822 A1 | 12/2016 | Fujimura et al. |
| 2022/0386868 A1 | 12/2022 | Ono |

FOREIGN PATENT DOCUMENTS

| | | |
|---|---|---|
| JP | 2011-147611 A | 8/2011 |
| JP | 2013-226383 A | 11/2013 |
| JP | 2013-248376 A | 12/2013 |
| JP | 2014-500096 A | 1/2014 |
| JP | 2015-43814 A | 3/2015 |
| JP | 2015-506772 A | 3/2015 |
| JP | 2015-515894 A | 6/2015 |
| JP | 2015-160103 A | 9/2015 |
| JP | 2018-023675 A | 2/2018 |
| JP | 2019-88382 A | 6/2019 |
| WO | 2017/135278 A1 | 8/2017 |

OTHER PUBLICATIONS

Extended European Search Report issued Dec. 22, 2023, in corresponding European Patent Application No. 20916752.7, 11 pages.
Japanese Office Action issued Feb. 27, 2024, in corresponding Japanese Patent Application No. 2020-013119, 10 pages.
International Search Report and Written Opinion mailed on Feb. 16, 2021, received for PCT Application PCT/JP2020/047607, Filed on Dec. 21, 2020, 9 pages including English Translation.

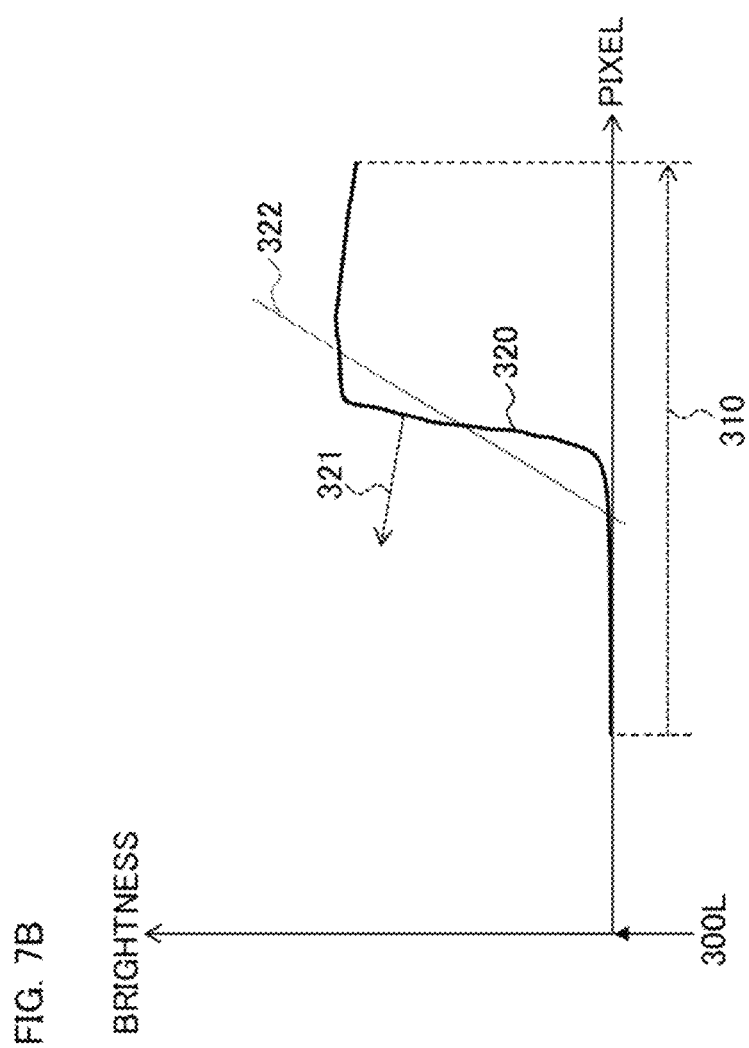

OPHTHALMIC APPARATUS, METHOD OF CONTROLLING THE SAME, AND RECORDING MEDIUM

CROSS-REFERENCE TO RELATED APPLICATIONS

This application is a national stage (under 35 U.S.C. 371) of International Patent Application No. PCT/JP2020/047607, filed Dec. 21, 2020, claiming priority to Japanese Patent Application No. 2020-013119, filed Jan. 30, 2020, both of which are herein incorporated by reference in their entirety.

TECHNICAL FIELD

The present disclosure relates generally to an ophthalmic apparatus, a method of controlling the same, and a recording medium.

BACKGROUND OF THE INVENTION

Anterior eye segment analysis techniques using optical coherence tomography (OCT) are known (see, for example, Patent Documents 1 to 5). It is sometimes desirable to perform scanning of a wide area of an anterior eye segment at a time for OCT anterior eye segment analysis. However, there also are cases in which a part of an anterior eye segment is not imaged due to limitations in the imaging range in the depth direction.

For example, some techniques of corner angle analysis are performed by applying a wide-area B-scan (e.g., a B-scan with the scan length of 16 mm) to the anterior eye segment; however, a part (central part) of a cornea is sometimes not imaged within an OCT image frame (see, for example, FIG. 1). Corner angle analysis or other analysis techniques performs correction of image distortion caused by corneal refractive power etc. in order to grasp the morphology (e.g., shape, dimensions, or the like) of a tissue with high accuracy. However, as shown in FIG. 1, refraction correction cannot be conducted in the case where an image of a part of the cornea is missing.

PATENT DOCUMENT 1: Japanese Unexamined Patent Application Publication No. 2011-147611
PATENT DOCUMENT 2: Japanese Unexamined Patent Application Publication No. 2013-226383
PATENT DOCUMENT 3: Japanese Unexamined Patent Application Publication (Translation of PCT Application) No. 2014-500096
PATENT DOCUMENT 4: Japanese Unexamined Patent Application Publication No. 2015-43814
PATENT DOCUMENT 5: WO 2017/135278

BRIEF SUMMARY OF THE INVENTION

An object of the present disclosure is to provide a technique that is capable of performing refraction correction even when a part of a cornea is not imaged.

Means for Solving the Problem

An ophthalmic apparatus according to some aspect examples includes: an image acquiring unit configured to acquire an anterior segment image constructed based on data collected from an anterior segment of a subject's eye by optical coherence tomography (OCT) scanning, the anterior segment image including a missing part corresponding to a part of a cornea; a corneal shape estimating processor configured to estimate a shape of the missing part of a cornea image by analyzing the anterior segment image acquired by the image acquiring unit; and a first image correcting processor configured to correct distortion of the anterior segment image based at least on the shape of the missing part estimated by the corneal shape estimating processor.

In an ophthalmic apparatus according to some aspect examples, the corneal shape estimating processor may include an anterior corneal surface region identifying processor configured to identify an anterior corneal surface region corresponding to an anterior surface of the cornea by analyzing the anterior segment image, and the corneal shape estimating processor may further be configured to perform estimation of the shape of the missing part based at least on the anterior corneal surface region identified by the anterior corneal surface region identifying processor.

In an ophthalmic apparatus according to some aspect examples, the corneal shape estimating processor may further include a curve fitting processor configured to apply curve fitting to the anterior corneal surface region identified by the anterior corneal surface region identifying processor to derive an approximate curve of the anterior corneal surface region of the cornea image including the missing part.

In an ophthalmic apparatus according to some aspect examples, the curve fitting processor may further be configured to apply, to the anterior corneal surface region, curve fitting based on a robust estimation algorithm for removing an outlier.

In an ophthalmic apparatus according to some aspect examples, the robust estimation algorithm may include a random sample consensus (RANSAC) algorithm.

In an ophthalmic apparatus according to some aspect examples, the first image correcting processor may further be configured to perform correction of the distortion of the anterior segment image based at least on the approximate curve.

In an ophthalmic apparatus according to some aspect examples, the anterior corneal surface region identifying processor may further be configured to perform identification of the anterior corneal surface region by applying edge detection to the anterior segment image.

In an ophthalmic apparatus according to some aspect examples, the anterior corneal surface region identifying processor may further be configured to perform the identification of the anterior corneal surface region by identifying an edge where a gradient direction is toward a frame edge of the anterior segment image and where a gradient value is equal to or greater than a predetermined threshold value.

An ophthalmic apparatus according to some aspect examples may further include a second image correcting processor configured to correct a pixel aspect ratio of the anterior segment image.

In an ophthalmic apparatus according to some aspect examples, the second image correcting processor may further be configured to perform correction of the pixel aspect ratio of the anterior segment image whose distortion has been corrected by the first image correcting processor.

An ophthalmic apparatus according to some aspect examples may further include an analyzing processor configured to perform calculation of a predetermined anterior segment parameter by analyzing the anterior segment image whose distortion has been corrected by the first image correcting processor and whose pixel aspect ratio has been corrected by the second image correcting processor.

In an ophthalmic apparatus according to some aspect examples, the analyzing processor may include a corner angle analyzing processor configured to perform calculation of a predetermined corner angle parameter by analyzing the anterior segment image whose distortion has been corrected by the first image correcting processor and whose pixel aspect ratio has been corrected by the second image correcting processor.

In an ophthalmic apparatus according to some aspect examples, the image acquiring unit may include: a data collector configured to collect data by applying OCT scanning to the anterior segment; and an image constructing processor configured to construct the anterior segment image based on the data collected by the data collector.

In an ophthalmic apparatus according to some aspect examples, the image acquiring unit may include a receiver that receives the anterior segment image from outside.

A method according to some aspect examples is a method of controlling an ophthalmic apparatus that includes: causing the processor to acquire an anterior segment image constructed based on data collected from an anterior segment of a subject's eye by optical coherence tomography (OCT) scanning, the anterior segment image including a missing part corresponding to a part of a cornea; causing the processor to estimate a shape of the missing part of a cornea image by analyzing the anterior segment image; and causing the processor to correct distortion of the anterior segment image based at least on the shape of the missing part.

A recording medium according to some aspect examples is a computer-readable non-transitory recording medium that stores a program that causes a computer to execute a method according to some aspect examples.

Effect of the Invention

The aspect examples are capable of performing refraction correction even when a part of a cornea is not imaged.

BRIEF DESCRIPTION OF THE SEVERAL VIEWS OF THE DRAWING

FIG. 7B is a diagram illustrating an example of processing executed by an ophthalmic apparatus according to an aspect example.

DETAILED DESCRIPTION OF THE INVENTION

Figure 1:
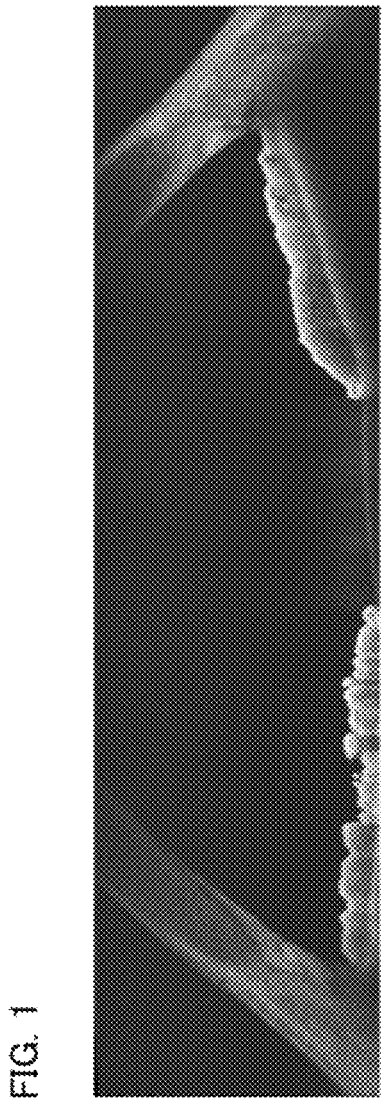
FIG. 1 illustrates an example of an anterior segment OCT image in which a central part of a cornea is not imaged.

The present disclosure describes several aspect examples of embodiments of an ophthalmic apparatus, a method of controlling the same, a program, and a recording medium with referring to the drawings. Any matters and items disclosed by the documents cited in the present disclosure and any other known technologies and techniques may be incorporated with the aspect examples described in the present disclosure. Note that "image data" and an "image" formed based on this image data are not distinguished in the present disclosure unless otherwise mentioned. Similarly, a "site (part, tissue, etc.)" of a subject's eye and an "image" of this site are not distinguished in the present disclosure unless otherwise mentioned.

An ophthalmic apparatus according to some aspect examples is configured to be capable of measuring and imaging the anterior segment of a living eye by applying Fourier domain OCT techniques (e.g., swept source OCT techniques). The types of OCT techniques applicable to aspect examples are not limited to swept source OCT techniques, and spectral domain OCT techniques or time domain OCT techniques may be applied to some aspect examples.

An ophthalmic apparatus according to some aspect examples may be configured to be capable of executing processing of an image acquired by a modality other than OCT. For example, some aspect examples may be configured to be capable of executing processing of an image acquired by any of a fundus camera (retinal camera), a laser scanning ophthalmoscope (SLO), a slit lamp microscope, and an ophthalmic surgical microscope. An ophthalmic apparatus according to some aspect examples may include one or more of a fundus camera, an SLO, a slit lamp microscope, and an ophthalmic surgical microscope.

An ophthalmic apparatus according to some aspect examples is configured to acquire an image constructed based on data collected from the anterior segment of a living eye by applying OCT scanning, and to apply processing to this image. This image is referred to as an anterior segment image. An anterior segment image does not provide an image (representation) of the entire anterior segment, and at least a part of a cornea is not imaged (not represented). Typically, a central part of a cornea is missing as shown in FIG. 1.

In some aspect examples, the method and technique of acquiring an anterior segment image is freely selected. For example, an ophthalmic apparatus according to some aspect examples may include a configuration of collecting data by applying OCT scanning to the anterior segment of a living eye and a configuration of constructing an anterior segment image based on the data collected.

An ophthalmic apparatus according to some aspect examples may have a function of receiving an anterior segment image of a living eye from outside. In some examples, an anterior segment image of a living eye is acquired by using an OCT apparatus and this anterior segment image is stored in a medical image management system such as a picture archiving and communication system (PACS). An ophthalmic apparatus according to some aspect examples is configured to access to the medical image management system and obtain an anterior segment image.

In addition to descriptions of such an ophthalmic apparatus, the present disclosure gives descriptions of a method of controlling an ophthalmic apparatus, descriptions of a program of causing a computer to execute such a method, and descriptions of a recording medium storing such a program.

At least one or more of the functions of the elements described in the present disclosure are implemented by using a circuit configuration (circuitry) or a processing circuit configuration (processing circuitry). The circuitry or the processing circuitry includes any of the followings, all of which are configured and/or programmed to execute at least one or more functions disclosed herein: a general purpose processor, a dedicated processor, an integrated circuit, a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), an existing or conventional circuit configuration or circuitry, and any combination of these. A processor is considered to be processing circuitry or circuitry that includes a transistor and/or another circuitry. In the present disclosure, circuitry, a unit, a means, or a term similar to these is hardware that executes at least one or more functions disclosed herein, or hardware that is programmed to execute at least one or more functions disclosed herein. Hardware may be the hardware disclosed herein, or alternatively, known hardware that is programmed and/or configured to execute at least one or more functions described herein. In the case where the hardware is a processor, which may be considered as a certain type of circuitry, then circuitry, a unit, a means, or a term similar to these is a combination of hardware and software. In this case, the software is used to configure the hardware and/or the processor.

<Configuration of Ophthalmic Apparatus>

Figure 2:
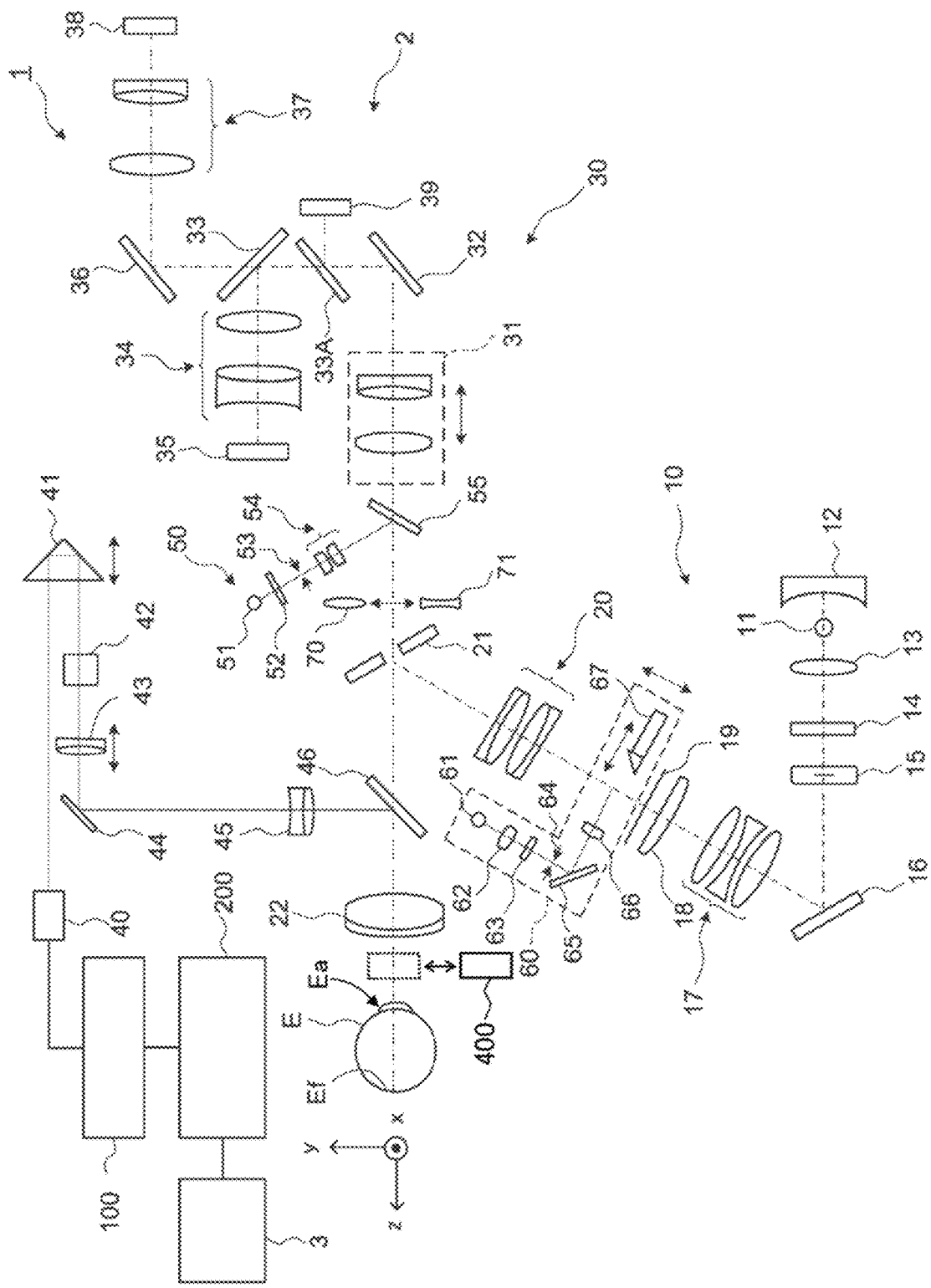
FIG. 2 is a diagram of an example of a configuration of an ophthalmic apparatus according to an aspect example.

The ophthalmic apparatus 1 of an aspect example shown in FIG. 2 is a multifunction apparatus that is a combination of an OCT apparatus and a fundus camera, and has both the function of applying OCT scanning to an anterior eye segment and the function of conducting photography of an anterior eye segment. The ophthalmic apparatus 1 includes the fundus camera unit 2, the OCT unit 100, and the arithmetic and control unit 200. The fundus camera unit 2 is provided with an element group (e.g., optical elements, mechanisms, etc.) for acquiring a front image of a subject's eye. The OCT unit 100 includes part of an element group (e.g., optical elements, mechanisms, etc.) for conducting OCT scanning. Another part of the element group for conducting OCT scanning is provided in the fundus camera unit 2. The arithmetic and control unit 200 includes one or more processors configured and programmed to execute various processes (e.g., calculations, controls, etc.), and one or more storage devices (memories). In addition to these elements, the ophthalmic apparatus 1 may also include any elements and/or any units such as a member for supporting the face of the subject, an attachment for switching or changing sites of a subject's eye to which OCT scanning is applied. Here, examples of the member for supporting the face of the subject include a chin rest and a forehead rest.

A description is now given of some examples of the attachment for switching or changing sites of a subject's eye to which OCT scanning is applied. An example attachment includes a lens group (lens unit). The anterior segment OCT attachment 400 (the attachment for anterior segment OCT 400) includes a lens group used for switching sites of the subject's eye E to which OCT scanning is applied between the posterior segment and the anterior segment. The anterior segment OCT attachment 400 may have the same configuration as the optical unit disclosed in Japanese Unexamined Patent Application Publication No. 2015-160103.

As illustrated in FIG. 2, the anterior segment OCT attachment 400 is inserted between the objective lens 22 and the subject's eye E. In the state in which the anterior segment OCT attachment 400 is placed in the optical path, the ophthalmic apparatus 1 can apply OCT scanning to the anterior segment of the subject's eye E. On the other hand, in the state in which the anterior segment OCT attachment 400 is removed from the optical path, the ophthalmic apparatus 1 can apply OCT scanning to the posterior segment of the subject's eye E. The movement (insertion and removal) of the anterior segment OCT attachment 400 is performed by hand or by machine (manually or automatically).

An ophthalmic apparatus of some aspect examples may be configured to apply OCT scanning to a posterior segment in the state in which an attachment is inserted in an optical path and to apply OCT scanning to an anterior segment in the state in which this attachment is removed from this optical path. Sites of a subject's eye to which OCT scanning is applied switched by an attachment are not limited to the combination of anterior segment and posterior segment, and may be any combinations of ocular sites. Also, a configuration for switching sites of a subject's eye to which OCT scanning is applied is not limited to attachments like the one described above (lens group, lens unit, optical unit), and some examples of this configuration may include one or more lenses movable along an optical path.

<Fundus Camera Unit 2>

The fundus camera unit 2 includes elements (e.g., optical elements, mechanisms, etc.) for acquiring digital images (digital photographs, digital pictures) by conducting photography of the subject's eye E (e.g., the anterior segment Ea, fundus Ef, etc.). The digital images of the subject's eye E acquired are front images (en face images) such as observation images and photographed images. An observation image is obtained, for example, by capturing a moving image using near-infrared light, and may be used for alignment, focusing, tracking, and other operations. A photographed image is a still image obtained using visible flash light or infrared flash light, for example. A photographed image may be used for diagnosis, analysis, or other purposes.

The fundus camera unit 2 includes the illumination optical system 10 and the photographing optical system 30. The illumination optical system 10 projects illumination light onto the subject's eye E. The photographing optical system 30 detects return light of the illumination light from the subject's eye E. Measurement light entered from the OCT unit 100 is directed to the subject's eye E through an optical path in the fundus camera unit 2, and return light of this measurement light from the subject's eye E is directed to the OCT unit 100 through the same optical path.

Light emitted by the observation light source 11 of the illumination optical system 10 (referred to as observation illumination light) is reflected by the concave mirror 12, passes through the condenser lens 13, and becomes near-infrared light after passing through the visible cut filter 14. Further, the observation illumination light is once converged at a location near the photographing light source 15, reflected by the mirror 16, and passes through the relay lens system 17, the relay lens 18, the diaphragm 19, and the relay lens system 20. Then, the observation illumination light is reflected on the peripheral part (i.e., the area surrounding the aperture part) of the aperture mirror 21, penetrates the dichroic mirror 46, and refracted by the objective lens 22, thereby illuminating the subject's eye E. Return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Furthermore, the return light of the observation illumination light passes through the half mirror 33A, is reflected by the dichroic mirror 33, and forms an image on the light receiving surface of the image sensor 35 by the imaging lens 34. The image sensor 35 detects the return light at a predetermined frame rate. The photographing optical system 30 is adjusted to be focused on the fundus Ef or the anterior eye segment Ea.

Light emitted by the photographing light source 15 (referred to as photographing illumination light) passes through the same route as the route of the observation illumination light and is projected onto the subject's eye E. Return light of the photographing illumination light from the subject's eye E passes through the same route as the route of the return light of the observation illumination light to the dichroic mirror 33, passes through the dichroic mirror 33, is reflected by the mirror 36, and forms an image on the light receiving surface of the image sensor 38 by the imaging lens 37.

The liquid crystal display (LCD) 39 displays a fixation target (fixation target image). Part of a light beam output from the LCD 39 is reflected by the half mirror 33A and the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

Varying the display position of the fixation target image on the LCD 39 can be used to change fixation position (also referred to as fixation direction) of the subject's eye E by the fixation target. That is, the line of sight of the subject's eye E can be guided in a desired direction by changing the fixation position. The ophthalmic apparatus 1 may be provided with a graphical user interface (GUI) used for designation of a desired fixation position.

Configurations for presenting, to the subject's eye E, a fixation target in such a manner that a fixation position can be changed, are not limited to a display device such as LCD. For example, a fixation matrix may be used, in place of such a display device, that includes a plurality of light emitting elements (e.g., light emitting diodes or the like) arranged in a matrix pattern (array pattern). In this example case, a fixation position can be changed by selecting and turning on a light emitting element. In another example case, a fixation position can be changed by means of one or more movable light emitting elements.

The alignment optical system 50 generates an alignment indicator used for alignment of the optical system with respect to the subject's eye E. Alignment light emitted by the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. Return light of the alignment light from the subject's eye E passes through the same route as the route of the return light of the observation illumination light and is guided to the image sensor 35. An image detected by the image sensor 35 (alignment indicator image) is used for performing manual alignment and/or automatic alignment.

As in existing or conventional techniques, the alignment indicator image of the present example includes two bright spot images whose positions change depending on alignment states (alignment conditions). When the relative position between the subject's eye E and the optical system changes in the xy direction, the two bright spot images are shifted together in the xy direction. When the relative position between the subject's eye E and the optical system changes in the z direction, the relative position (the distance) between the two bright spot images changes. In the state in which the distance between the subject's eye E and the optical system in the z direction matches with a working distance set in advance, the two bright spot images overlap each other. In the state in which the position of the subject's eye E matches with the position of the optical system in the xy direction, the two bright spot images are located within or near an alignment target set in advance. In the state in which not only the distance between the subject's eye E and the optical system in the z direction matches with the working distance but also the position of the subject's eye E matches with the position of the optical system in the xy direction, the two bright spot images overlap each other and are located within the alignment target.

When conducting automatic alignment, the data processor 230 detects the positions of the two bright spot images, and the main controller 211 controls the movement mechanism 150 (described later) on the basis of the positional relationship between the two bright spot images and the alignment target. When conducting manual alignment, the main controller 211 displays the two bright spot images together with an observation image of the subject's eye E on the display 241, and the user manipulates the operation device 242 to operate the movement mechanism 150 while monitoring the two bright spot images displayed.

The methods and techniques of alignment are not limited to those described above. An ophthalmic apparatus according to some aspect examples may include an alignment unit configured to perform the following processes (see, for example, Japanese Unexamined Patent Application Publication No. 2013-248376): a process of acquiring two or more photographed images of an anterior segment of an subject's eye by substantially simultaneously conducting two or more operations of anterior segment photography of the anterior segment from two or more different directions; a process of calculating a three dimensional position of the subject's eye by analyzing the two or more photographed images; and a process of moving an optical system based on the three dimensional position calculated.

The focusing optical system 60 generates a split indicator used for focus adjustment (focusing, focusing operation)

with respect to the subject's eye E. The focusing optical system 60 is moved along the optical path of the illumination optical system 10 in conjunction with movement of the photography focusing lens 31 along the optical path of the photographing optical system 30. The optical path of the illumination optical system 10 is referred to as the illumination optical path, and the optical path of the photographing optical system 30 is referred to as the photographing optical path. The reflection rod 67 is inserted into and removed from the illumination optical path. The reflective surface of the reflection rod 67 is inserted into the illumination optical path and placed in an oblique orientation before performing focus adjustment. Focus light emitted by the LED 61 passes through the relay lens 62, is split into two light beams by the split indicator plate 63, and passes through the two-hole diaphragm 64. The focus light, then, is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. Return light of the focus light from the subject's eye E passes through the same route as the route of the return light of the alignment light and is guided to the image sensor 35. An image detected by the image sensor 35 (split indicator image) is used for performing manual focusing and/or automatic focusing.

The diopter correction lenses 70 and 71 are selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for digital photography and the optical path for OCT scanning. The optical path for digital photography includes the illumination optical path and the photographing optical path. The optical path for OCT scanning is referred to as a sample arm. The dichroic mirror 46 reflects light of wavelength bands used for OCT scanning while transmitting light for digital photography. Listed from the OCT unit 100 side, the sample arm includes the collimator lens unit 40, the retroreflector 41, the dispersion compensation member 42, the OCT focusing lens 43, the optical scanner 44, and the relay lens 45.

The retroreflector 41 is movable in the directions indicated by the arrow in FIG. 2. These directions are the direction in which the measurement light LS is incident onto the subject's eye E and the direction in which return light of the measurement light LS from the subject's eye E travels. With this movement of the retroreflector 41, the length of the sample arm is changed. This change in the sample arm length may be used for operations such as optical path length correction on the basis of eye axial length, optical path length correction on the basis of corneal shape and/or eye fundus shape, and adjustment or regulation of interference conditions or states.

The dispersion compensation member 42, together with the dispersion compensation member 113 (described later) arranged in the reference arm, acts to equalize the dispersion characteristics of the measurement light LS and the dispersion characteristics of the reference light LR with each other.

The OCT focusing lens 43 is movable in the directions indicated by the arrow in FIG. 2 (that is, movable along the optical axis of the sample arm) in order to perform focus adjustment of the sample arm. With this movement of the OCT focusing lens 43, the focus conditions or the focus states (focal position, focal length) of the sample arm is changed. The ophthalmic apparatus 1 may be configured to be capable of executing interlocking control between the movement of the photography focusing lens 31, the movement of the focusing optical system 60, and the movement of the OCT focusing lens 43.

The optical scanner 44 is placed substantially at a position optically conjugate with the pupil of the subject's eye E. The optical scanner 44 deflects the measurement light LS guided by the sample arm. The optical scanner 44 of some examples may be a deflection system capable of two dimensional scanning that includes a deflector for performing scanning in the x direction and a deflector for performing scanning in the y direction (x-scanner and y-scanner). The optical scanner 44 of some examples may be a galvanometer scanner including two galvanometer mirrors. In some typical examples, one of the two deflectors is arranged at a position optically conjugate with the pupil of the subject's eye E, or the position optically conjugate with the pupil is arranged at a position between the two deflectors. Such arrangement makes it capable of OCT scanning of the fundus Ef in which the measurement light LS is deflected around a pivot located at a position in (or near) the pupil of the subject's eye E, which makes it possible to apply OCT scanning to a wide (broad) area of the fundus Ef.

In the present aspect, the optical scanner 44 is placed at a position substantially optically conjugate with the pupil of the subject's eye E as described above when the anterior segment OCT attachment 400 is not placed in the optical path. On the other hand, the optical scanner 44 is placed at a position substantially optically conjugate with a position between the anterior segment Ea and the anterior segment OCT attachment 400 when the anterior segment OCT attachment 400 is placed in the optical path. More specifically, in the case in which the anterior segment OCT attachment 400 is removed from the optical path, for example, one of the x-scanner and the y-scanner is placed at a position substantially optically conjugate with the pupil, or a position between the x-scanner and the y-scanner is placed at a position substantially optically conjugate with the pupil. Further, in the case in which the anterior segment OCT attachment 400 is inserted in the optical path, for example, one of the x-scanner and the y-scanner is placed at a position substantially optically conjugate with a position between the anterior segment Ea and the anterior segment OCT attachment 400, or a position between the x-scanner and the y-scanner is placed at a position substantially optically conjugate with a position between the anterior segment Ea and the anterior segment OCT attachment 400.

<OCT Unit 100>

Figure 3:
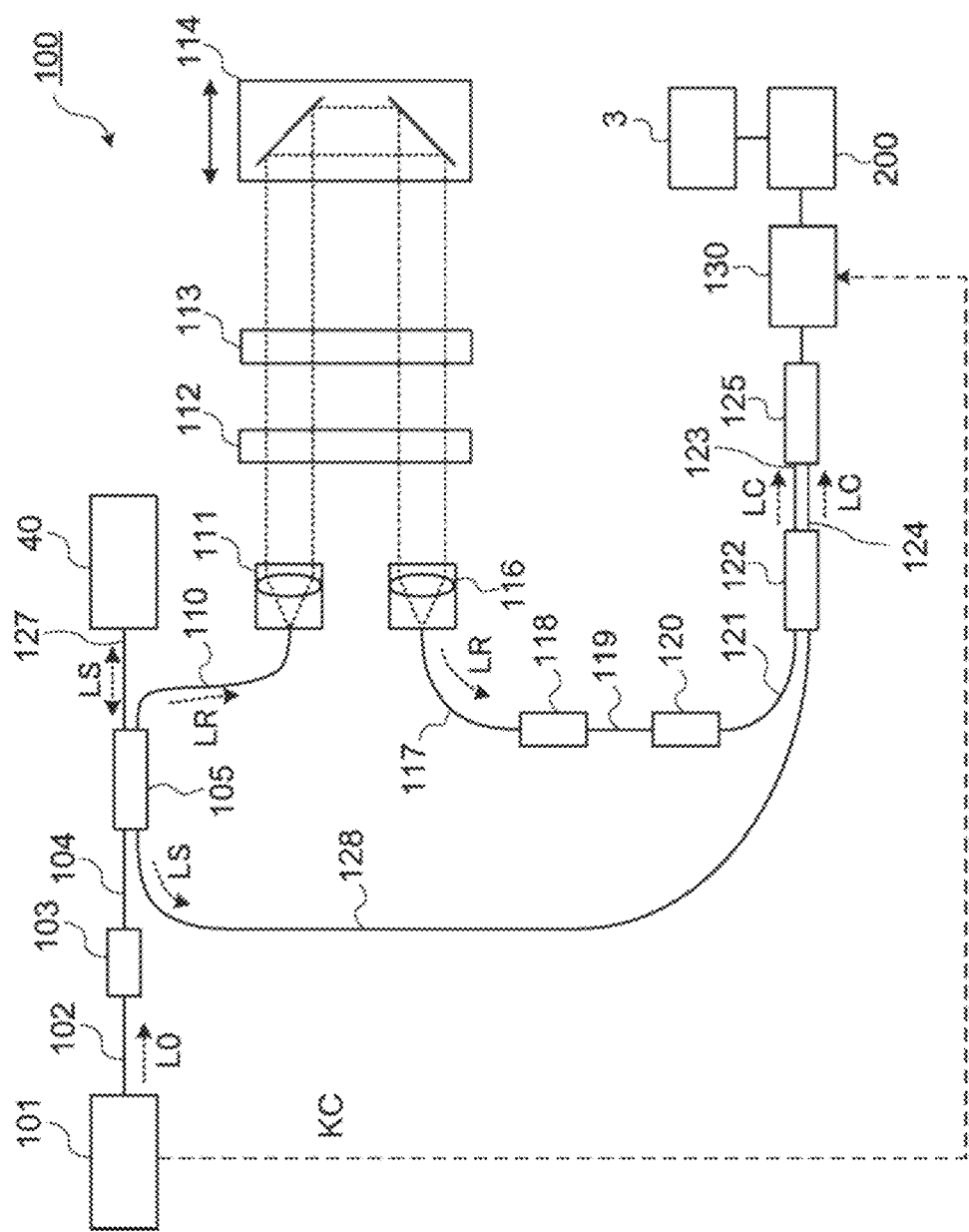
FIG. 3 is a diagram of an example of a configuration of an ophthalmic apparatus according to an aspect example.

As illustrated in FIG. 3, the OCT unit 100 is provided with an optical system and mechanisms for performing swept source OCT. This optical system includes an interference optical system. This interference optical system is configured to split light emitted by a wavelength tunable light source (wavelength sweeping light source) into measurement light and reference light, to generate interference light by superposing return light of the measurement light from the subject's eye E on the reference light that has been guided by a reference optical path (reference arm), and to detect this interference light. A result of this interference light detection (detection signal) obtained by the interference optical system, is a signal representing a spectrum of the interference light. This detection signal is sent to the arithmetic and control unit 200 (the image data constructing unit 220).

The light source unit 101 of some examples includes a near-infrared wavelength tunable laser configured to vary the wavelengths of emitted light at high speed. The light L0 output from the light source unit 101 is guided to the polarization controller 103 through the optical fiber 102. The polarization controller 103 is configured to perform regulation (adjustment) of the polarization condition (polarization state) of the light L0. Further, the light L0 is guided to the fiber coupler 105 through the optical fiber 104. The fiber coupler 105 is configured to split the light L0 into the measurement light LS and the reference light LR. The optical path of the measurement light LS is referred to as the sample arm or the like, and the optical path of the reference light LR is referred to as the reference arm or the like.

The reference light LR is guided through the optical fiber 110 to the collimator 111, is converted into a parallel light beam by the collimator 111, travels through the optical path length correction member 112 and the dispersion compensation member 113, and is guided to the retroreflector 114. The optical path length correction member 112 is an optical element for equalizing the optical path length of the reference light LR and the optical path length of the measurement light LS with each other. The dispersion compensation member 113 is an optical element for equalizing the dispersion characteristics of the reference light LR and the dispersion characteristics of the measurement light LS with each other, together with the dispersion compensation member 42 disposed in the sample arm. The retroreflector 114 is movable along the optical path of the reference light LR that is incident onto the retroreflector 114. With this, the length of the reference arm is changed. This change in the reference arm length may be used for operations such as optical path length correction on the basis of eye axial length, optical path length correction on the basis of corneal shape and/or eye fundus shape, and adjustment or regulation of interference conditions or states.

The reference light LR that has passed through the retroreflector 114 travels through the dispersion compensation member 113 and the optical path length correction member 112, is converted from a parallel light beam to a convergent light beam by the collimator 116, and is incident onto the optical fiber 117. The reference light LR that has entered the optical fiber 117 is guided to the polarization controller 118, and the polarization state of the reference light LR is regulated by the polarization controller 118. The polarization controller 118 is an optical device for interference condition regulation (interference condition adjustment, interference state regulation, interference state adjustment). The polarization controller 118 is used for optimizing the strength of interference (coherence) between the measurement light LS and the reference light LR, for example. The reference light LR output from the polarization controller 118 is guided to the attenuator 120 through the optical fiber 119, and the amount of light of the reference light LR is regulated by the attenuator 120. Subsequently, the reference light LR is guided to the fiber coupler 122 through the optical fiber 121.

Meanwhile, the measurement light LS generated by the fiber coupler 105 is guided through the optical fiber 127 to the collimator lens unit 40 and is converted to a parallel light beam by the collimator lens unit 40. The measurement light LS output from the collimator lens unit 40 passes through the retroreflector 41, the dispersion compensation member 42, the OCT focusing lens 43, the optical scanner 44, and the relay lens 45, is reflected by the dichroic mirror 46, and is refracted by the objective lens 22, thereby being projected onto the subject's eye E. The measurement light LS is reflected and scattered at various depth positions of the subject's eye E. Return light of the measurement light LS from the subject's eye E travels along the same route as the outward way in the opposite direction to the fiber coupler 105, and then reaches the fiber coupler 122 through the optical fiber 128.

The fiber coupler 122 superposes the measurement light LS reached here through the optical fiber 128 with the reference light LR reached here through the optical fiber 121 to generate interference light. The fiber coupler 122 splits the interference light generated by the fiber coupler 122 at a predetermined splitting ratio (e.g., 1 to 1) to generate a pair of interference light LC. The pair of interference light LC is guided to the detector 125 through the optical fibers 123 and 124, respectively.

The detector 125 of some examples includes a balanced photo diode. This balanced photodiode includes a pair of photodetectors that detects the pair of the interference light LC respectively. The balanced photodiode outputs a difference signal between a pair of detection signals corresponding to the pair of the interference light LC respectively obtained by the pair of photodetectors. The detector 125 sends this output (difference signal, detection signal) to the data acquisition system (DAQ) 130.

The clock KC is supplied from the light source unit 101 to the data acquisition system 130. The clock KC is generated in the light source unit 101 in synchronization with the output timings of individual wavelengths varied over a predetermined wavelength range by the wavelength tunable light source. The light source unit 101 of some examples is configured to split the light L0 of the individual output wavelengths to generate two pieces of split light, to apply an optical delay to one of the two pieces of split light, to superpose the resulting two pieces of split light with one another, to detect the resulting superposed light, and to generate the clock KC based on the detection result of the superposed light. Based on the clock KC, the data acquisition system 130 performs sampling of the detection signal input from the detector 125. The data acquisition system 130 sends the result of this sampling to the arithmetic and control unit 200.

The present aspect example is provided with both an element for changing the sample arm length (e.g., the retroreflector 41) and an element for changing the reference arm length (e.g., the retroreflector 114 or a reference mirror). However, some other aspect examples may be provided with only either one of these two elements. An element for changing the difference between the sample arm length and the reference arm length (i.e., an element for changing the optical path length difference) is not limited to these examples described herein, and may be freely selected element such as any optical member and/or any mechanism.

As described above, swept source OCT is a technique including the following processes: a process of splitting light emitted by a wavelength tunable light source into measurement light and reference light; a process of generating interference light by superposing return light of the measurement light from a sample and the reference light; a process of detecting the interference light by a photodetector; and a process of constructing an image of the sample by applying signal processing including a Fourier transform to detection data collected corresponding to wavelength sweeping (change in emitted wavelengths) and scanning with the measurement light.

Spectral domain OCT, an alternative to swept source OCT, is a technique including the following processes: a process of splitting light emitted by a low coherence light source (broad band light source, wide band light source) into measurement light and reference light; a process of generating interference light by superposing return light of the measurement light from a sample and the reference light; a process of detecting a spectral distribution (spectral components) of the interference light by a spectrometer; and a process of constructing an image of the sample by applying signal processing including a Fourier transform to the spectral distribution detected.

In short, swept source OCT can be said to be an OCT technique of acquiring a spectral distribution of interference light in a time-divisional manner while spectral domain OCT can be said to be an OCT technique of acquiring a spectral distribution of interference light in a space-divisional manner.

<Control System and Processing System>

Figure 4:
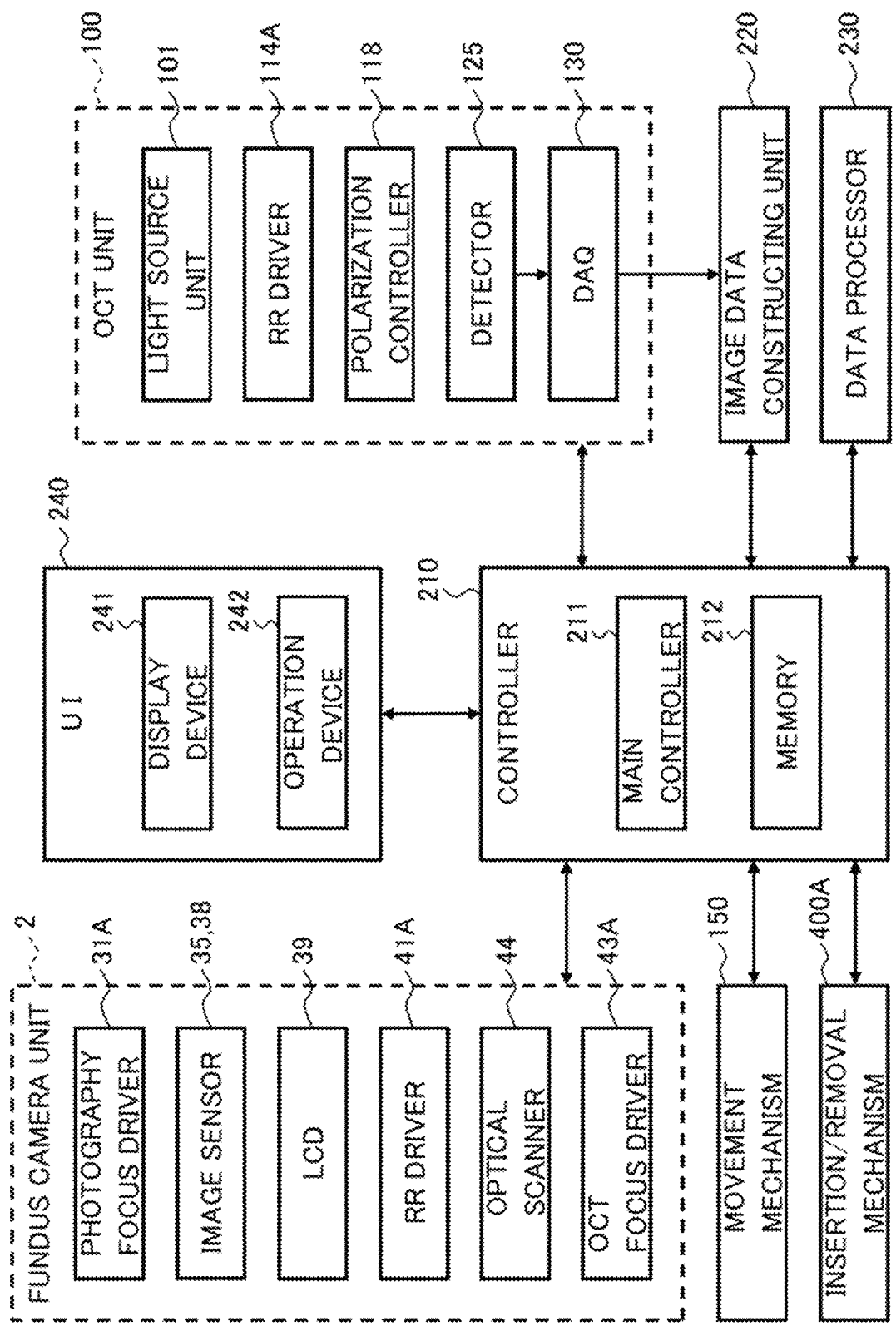
FIG. 4 is a diagram of an example of a configuration of an ophthalmic apparatus according to an aspect example.
Figure 5:
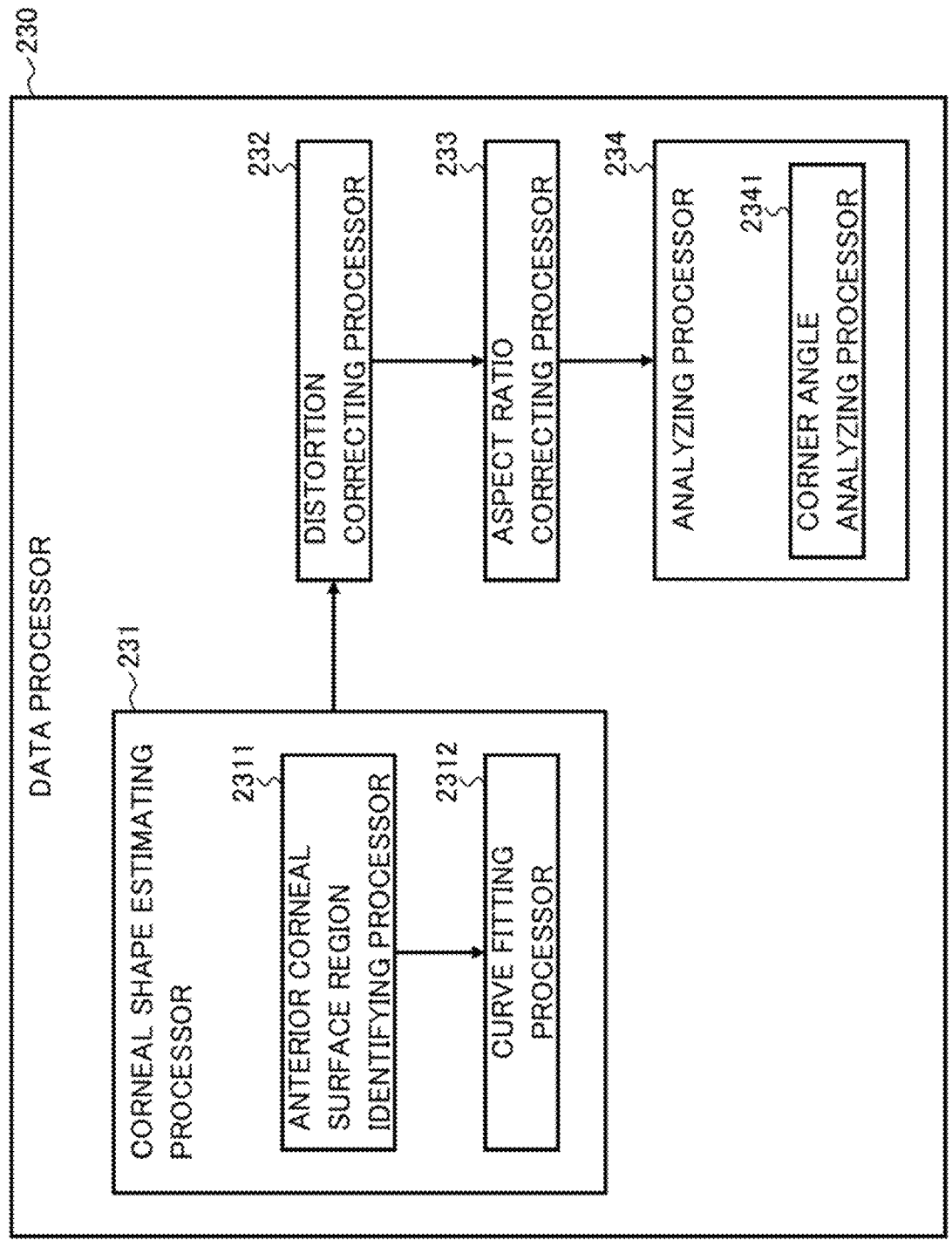
FIG. 5 is a diagram of an example of a configuration of an ophthalmic apparatus according to an aspect example.

FIG. 4 and FIG. 5 illustrate examples of the configurations of the control system and the processing system of the ophthalmic apparatus 1. The arithmetic and control unit 200 of some examples may include the controller 210, the image data constructing unit 220, and the data processor 230. The ophthalmic apparatus 1 may further include a communication device for performing data communication with external apparatuses. The ophthalmic apparatus 1 may further include a drive device (reader and/or writer) for reading out data from recording media and writing data into recording media.

<Controller 210>

The controller 210 performs various kinds of controls. The controller 210 includes the main controller 211 and the memory 212. The main controller 211 includes one or more processors and executes control of each element of the ophthalmic apparatus 1 (including the elements shown in FIG. 2 to FIG. 5). The main controller 211 is implemented by cooperation between hardware including the one or more processors and control software.

The photography focus driver 31A is configured to move the photography focusing lens 31 disposed in the photographing optical path and the focusing optical system 60 disposed in the illumination optical path under control of the main controller 211. The retroreflector driver (RR driver) 41A is configured to move the retroreflector 41 disposed in the sample arm under control of the main controller 211. The OCT focus driver 43A is configured to move the OCT focusing lens 43 disposed in the sample arm under control of the main controller 211. The retroreflector driver (RR driver) 114A is configured to move the retroreflector 114 disposed in the reference arm under control of the main controller 211. Each of the above drivers includes an actuator, such as a pulse motor, that operates under control of the main controller 211. The optical scanner 44 disposed in the sample arm also operates under control of the main controller 211.

The movement mechanism 150 of some examples is configured to move the fundus camera unit 2 in a three dimensional manner. The movement mechanism 150 of some typical examples includes the following elements: an x stage that is movable in the ±x directions (left and right directions); an x movement mechanism configured to move the x stage; a y stage that is movable in the ±y directions (upward and downward directions); a y movement mechanism configured to move the y stage; a z stage that is movable in the ±z directions (front and back directions, depth direction); and a z movement mechanism configured to move the z stage. Each of these movement mechanisms includes an actuator, such as a pulse motor, that operates under control of the main controller 211.

The insertion and removal mechanism 400A is configured to perform an operation of inserting the anterior segment OCT attachment 400 into the OCT optical path (sample arm), and an operation of removing the anterior segment OCT attachment 400 from the OCT optical path (sample arm). The insertion and removal mechanism 400A includes an actuator, such as a solenoid actuator, that operates under control of the main controller 211.

The memory 212 retains various kinds of data. Examples of data stored in the memory 212 include OCT images, digital images (anterior segment images, fundus images), subject's eye information, and analysis data. The subject's eye information includes subject information such as a patient identifier (patient ID) and a patient's name, identification information for right and left eyes, and electronic medical record information.

<Image Data Constructing Unit 220>

The image data constructing unit 220 includes one or more processors and is configured to construct OCT image data of the subject's eye E based on signals (sampling data) input from the data acquisition system 130. The OCT image data constructed by the image data constructing unit 220 is one or more pieces of A-scan image data, and typically is B-scan image data (two dimensional cross sectional image data, two dimensional tomographic image data) consisting of a plurality of pieces of A-scan image data.

The process of constructing OCT image data includes noise elimination (noise reduction), filtering, fast Fourier transform (FFT), and other processes, as in existing or conventional Fourier domain OCT techniques. In the cases in which other types of OCT techniques are employed, the image data constructing unit 220 executes known processing in accordance with an OCT technique employed.

The image data constructing unit 220 may be configured to construct three dimensional data of the subject's eye E based on signals input from the data acquisition system 130. This three dimensional data is three dimensional image data representing a three dimensional region (referred to as a volume) of the subject's eye E. This three dimensional image data is image data in which the positions of pixels are defined using a three dimensional coordinate system. Examples of such three dimensional image data include stack data and volume data.

Stack data is image data formed by arranging (disposing), in a three dimensional manner, a plurality of cross sectional images acquired along a plurality of scan lines, on the basis of the positional relationship between these scan lines. In other words, stack data is image data constructed by representing multiple cross sectional images, which are originally defined in individually different two dimensional coordinate systems, with a single three dimensional coordinate system, that is, by embedding the multiple cross sectional images into a single three dimensional space. In further other words, stack data is image data formed by arranging, in a three dimensional manner, a plurality of A-scan image data acquired respectively for a plurality of scan points arranged in a two dimensional manner (that is, for a scan point array), on the basis of the positional relationship between these scan points.

Volume data is image data whose elements (picture elements) are voxels arranged in a three dimensional manner. Volume data is also referred to as voxel data. volume data is constructed by applying processing such as interpolation and voxelization to stack data.

The image data constructing unit 220 constructs an image for display, by applying rendering to three dimensional image data. Examples of applicable rendering techniques include volume rendering, surface rendering, maximum intensity projection (MIP), minimum intensity projection (MinIP), and multi planar reconstruction (MPR).

The image data constructing unit 220 may be configured to construct an OCT front image (OCT en face image) based on three dimensional image data. The image data constructing unit 220 of some examples may be configured to construct projection data of three dimensional image data by applying, to the three dimensional image data, projection processing in the z direction (A-line direction, depth direction). Similarly, the image data constructing unit 220 may be configured to construct projection data from partial data of three dimensional image data such as a slab of three dimensional image.

In some typical examples, partial data of three dimensional image data, such as a slab, may be obtained by using segmentation processing. Segmentation, or image segmentation, is image processing of partitioning an image to identify a partial region. Segmentation of some typical examples is performed to identify an image region corresponding to a predetermined tissue of the subject's eye E. Segmentation of some examples may include any known image processing techniques, and may include, for example, image processing such as edge detection and/or a segmentation technique using machine learning (e.g., deep learning). Segmentation of the present aspect example is executed, for example, by the image data constructing unit 220 or the data processor 230.

The ophthalmic apparatus 1 may be capable of performing OCT motion contrast imaging. OCT motion contrast imaging is a technique of imaging motion of fluid (liquid) etc. in an eye (see, for example, Japanese Unexamined Patent Application Publication (Translation of PCT Application) No. 2015-515894).

The image data constructing unit 220 is implemented by cooperation between hardware including one or more processors and image data constructing software.

<Data Processor 230>

The data processor 230 includes one or more processors and is configured to perform various kinds of data processing on an image of the subject's eye E. The data processor 230 of some examples is implemented by cooperation between hardware including the one or more processors and data processing software.

The data processor 230 may be configured to perform position matching (registration) between two images acquired for the subject's eye E. The data processor 230 of some examples may be configured to perform registration between three dimensional image data acquired using OCT scanning and a front image (en face image) acquired by the fundus camera unit 2. The data processor 230 of some examples may be configured to perform registration between two OCT images acquired using OCT scanning. The data processor 230 of some examples may be configured to perform registration between two front images acquired by the fundus camera unit 2. The data processor 230 of some examples may be configured to apply registration to any of resulting data of analysis of one or more OCT images, resulting data of analysis of one or more front images, and other analysis results. Registration may be performed using freely selected known techniques. Registration of some examples may include feature point extraction and affine transformation.

The data processor 230 of some aspect examples, as shown in FIG. 5, includes the corneal shape estimating processor 231, the distortion correcting processor 232, the aspect ratio correcting processor 233, and the analyzing processor 234. Further, the corneal shape estimating processor 231 of some aspect examples includes the anterior corneal surface region identifying processor 2311 and the curve fitting processor 2312. In addition, the analyzing processor 234 of some aspect examples includes the corner angle analyzing processor 2341.

As mentioned above, the data processor 230 is configured to apply processing to an image of the anterior segment Ea acquired using OCT scanning. An anterior segment image to which the data processor 230 applies processing, does not depict the entire anterior segment Ea, and does not include an image corresponding to a central region of the cornea (that is, a region including the corneal apex and its neighborhood) as shown in FIG. 1.

<Corneal Shape Estimating Processor 231>

The corneal shape estimating processor 231 is configured to analyze an anterior segment image of the subject's eye E to estimate the shape of a missing part of a cornea image. The corneal shape estimating processor 231 of some typical examples may be configured to analyze an anterior segment image in which an image corresponding to a central part of a cornea image is missing as shown in FIG. 1, thereby estimating the shape of this central part.

A missing part of the cornea image is not limited to a central part, but may be, for example, a part that does not include the corneal apex (such a part that does not include the corneal apex is referred to as a peripheral part of the cornea). If this is the case, the corneal shape estimating processor 231 may estimate the shape of the peripheral part by analyzing an anterior segment image in which an image corresponding to the peripheral part of the cornea is not depicted.

The configuration and processing employed for such corneal shape estimation may be freely selected. The corneal shape estimating processor 231 of the present example is configured to execute corneal shape estimation by the anterior corneal surface region identifying processor 2311 and the curve fitting processor 2312.

The corneal shape estimating processor 231 is implemented by cooperation between hardware including one or more processors and corneal shape estimating software.

<Anterior Corneal Surface Region Identifying Processor 2311>

Figure 6:
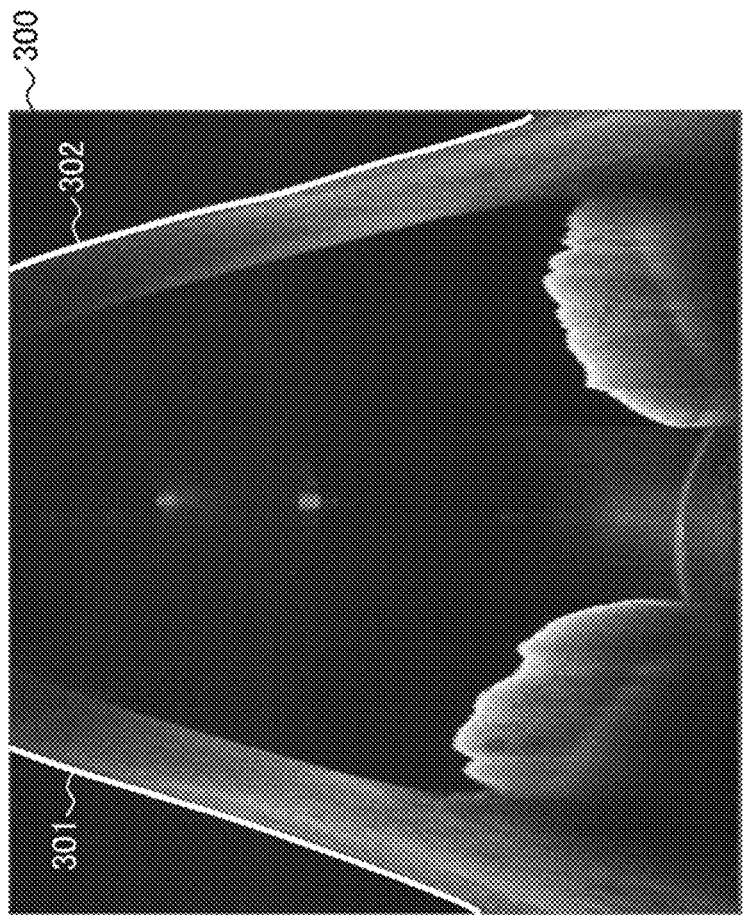
FIG. 6 is a diagram illustrating an example of processing executed by an ophthalmic apparatus according to an aspect example.

The anterior corneal surface region identifying processor 2311 is configured to identify an anterior corneal surface region corresponding to the anterior surface of the cornea by analyzing an anterior segment image of the subject's eye E. As shown in FIG. 6, the anterior corneal surface region identifying processor 2311 of some examples identifies the anterior corneal surface regions 301 and 302 by analyzing the anterior segment image 300 in which a central part of the cornea is not depicted.

The configuration and processing employed for such anterior corneal surface region identification may be freely selected. The anterior corneal surface region identifying processor 2311 of the present example is configured to execute anterior corneal surface region identification by applying edge detection to an anterior segment image.

Figure 7A:
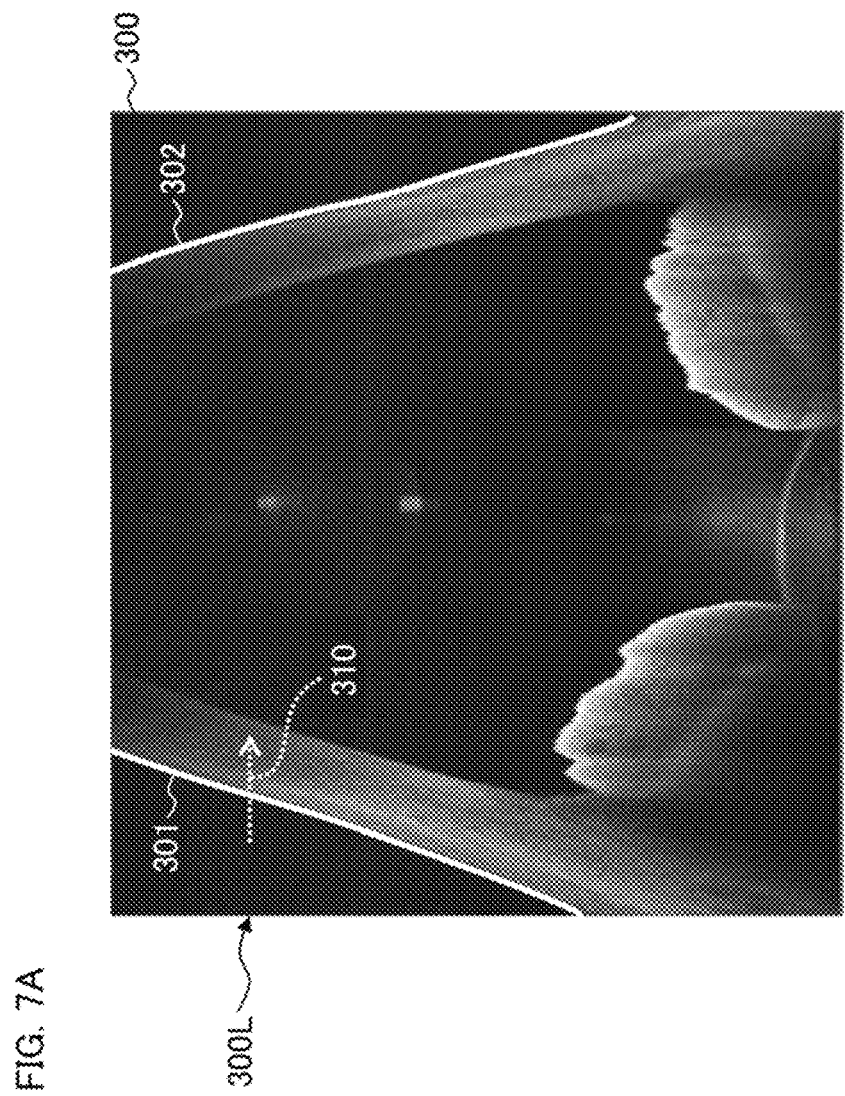
FIG. 7A is a diagram illustrating an example of processing executed by an ophthalmic apparatus according to an aspect example.

For example, the anterior corneal surface region identifying processor 2311 is configured to identify an anterior corneal surface region by detecting an edge where the gradient direction is toward a frame edge of the anterior segment image and where the gradient value (gradient intensity, gradient strength, gradient magnitude) is equal to or greater than a predetermined threshold value. An example of the anterior corneal surface region identification of the present example will now be described with referring to FIG. 7A and FIG. 7B. In this example, the anterior corneal surface region identifying processor 2311 analyzes the one dimensional region 310 shown in FIG. 7A. The one dimensional region 310 consists of an array of multiple pixels (see also FIG. 7B). The reference character 300L indicates the left edge of the frame of the anterior segment image 300. The reference character 320 in FIG. 7B indicates a brightness distribution graph for the plurality of pixels arranged in the one dimensional region 310. As can be seen from the shape of the brightness distribution graph 320, a portion of the brightness distribution graph 320 meets the following conditions: a condition that the gradient value of brightness is greater than the predetermined threshold value 322; and a condition that the normal direction (normal vector) 321 that indicates the direction of the gradient is toward the left edge 300L of the frame. A region with such gradients is detected as an edge. By applying such processing to various one dimensional regions, the anterior corneal surface region 301 can be identified. Similarly, the anterior corneal surface region 302 can be identified by searching a portion of the brightness distribution graph where the gradient value of brightness is greater than a predetermined threshold value and the normal direction that indicates the direction of the gradient is toward the right edge of the frame.

The anterior corneal surface region identifying processor 2311 is implemented by cooperation between hardware including one or more processors and anterior corneal surface region identifying software.

<Curve Fitting Processor 2312>

Figure 8:
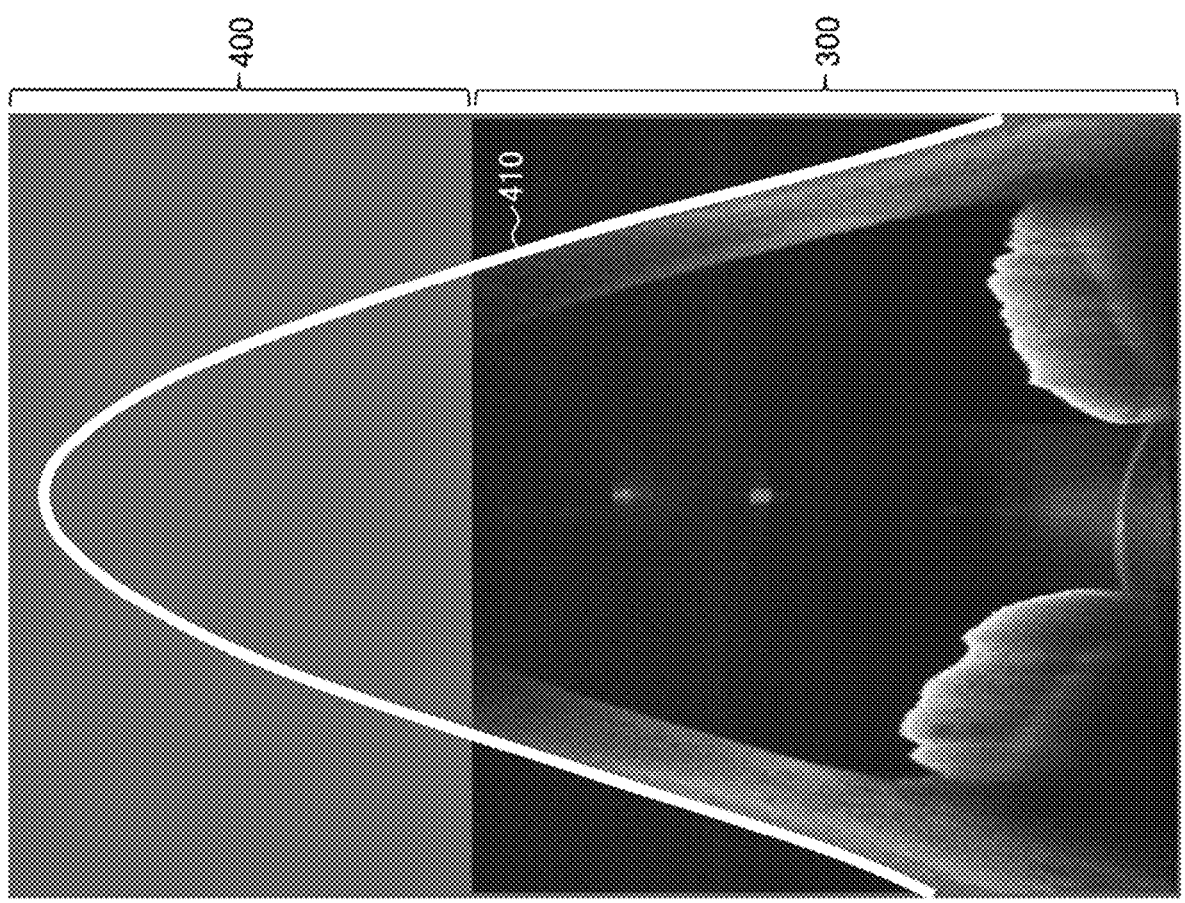
FIG. 8 is a diagram illustrating an example of processing executed by an ophthalmic apparatus according to an aspect example.

The curve fitting processor 2312 is configured to apply curve fitting to the anterior corneal surface region identified by the anterior corneal surface region identifying processor 2311, to derive an approximate curve of the anterior corneal surface region of the cornea image including the above-described missing part. In other words, the curve fitting processor 2312 is configured to estimate the morphology (shape) of the missing part that is not depicted in the anterior segment image, based on the anterior corneal surface region identified from the anterior segment image by the anterior corneal surface region identifying processor 2311. This curve fitting gives the approximate curve 410, shown in FIG. 8, that represents an estimated shape of the anterior surface of the cornea including the central part of the cornea (the missing part) that is not depicted in the anterior segment image 300. The reference character 400 in FIG. 8 indicates a virtual image frame that is an upward extension of the anterior segment image 300.

The curve fitting processor 2312 may be configured to apply, to the anterior corneal surface region, curve fitting on the basis of a robust estimation algorithm for removing an outlier. This robust estimation algorithm may include a random sample consensus (RANSAC) algorithm. By employing such a robust estimation algorithm, it becomes possible to remove an outlier(s) caused by noise or other factors, thereby performing curve fitting with a high degree of accuracy.

The curve fitting processor 2312 is implemented by cooperation between hardware including one or more processors and curve fitting software.

<Distortion Correcting Processor 232>

The distortion correcting processor 232 is configured to correct distortion of the anterior segment image based at least on the shape of the missing part estimated by the corneal shape estimating processor 231. The distortion correcting processor 232 of the present example may be configured to perform correction of the distortion of the anterior segment image based at least on the approximate curve derived by the curve fitting processor 2312. The image distortion correction executed by the distortion correcting processor 232 is image correction on the basis of the effect of refraction at the anterior surface of the cornea (refraction correction).

Figure 9:
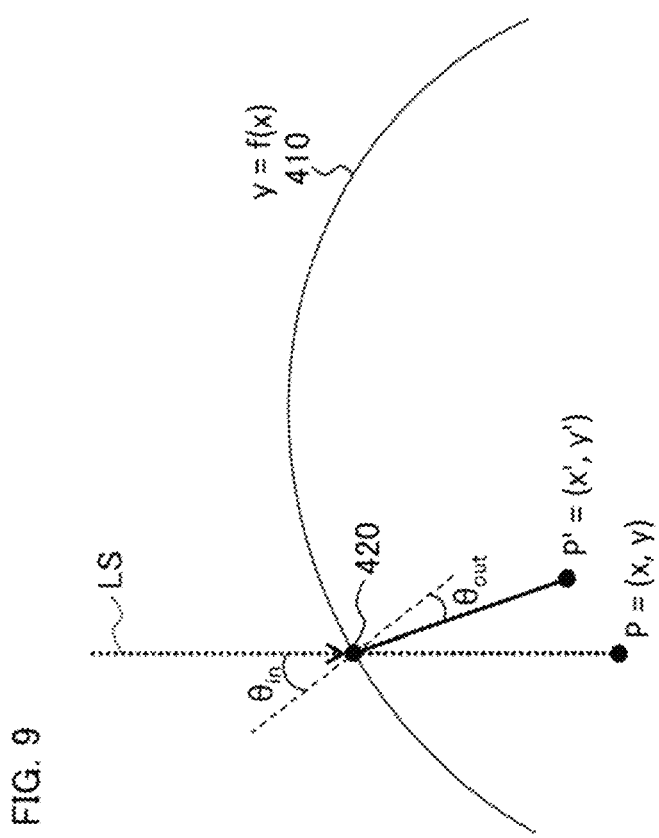
FIG. 9 is a diagram illustrating an example of processing executed by an ophthalmic apparatus according to an aspect example.

An example of the refraction correction will now be described with referring to FIG. 9. Let y=f(x) be the equation (mathematical expression) of the approximate curve derived by the curve fitting processor 2312. In addition, the value of the refractive index of air (e.g., 1.000292) and the value of the refractive index of the cornea (e.g., 1.376) are set.

The light beam (the measurement light LS) incident onto the point 420 on the anterior corneal surface 410 is now considered. Let $\theta_{in}$ be the angle of incidence of the measurement light LS at the point 420. Then, the angle of refraction Bout of the measurement light LS is derived from the angle of incidence $\theta_{in}$, the refractive index of air, and the refractive index of the cornea by Snell's law.

In addition, let $r_{air}$ be the distance per pixel (resolution) in air, let $r_{cor}$ be the distance per pixel (resolution) in cornea, and let $r_h$ be the quotient (ratio) of the length of a scan (e.g., 16 mm) over the number of pixels (e.g., 1024). Then, the function T=|f(x)−y| is considered.

Now, consider the point (pixel) P=(x, y) located at a position below the anterior corneal surface 410 in the anterior segment image 300 before distortion correction. That is, consider the point (pixel) P=(x, y) located at a position between the anterior corneal surface 410 and the lower edge of the frame in the anterior segment image 300 before distortion correction. Then, the point P'=(x', y') derived by applying refraction correction to the point P=(x, y) is expressed by the following equations: x'=T($r_{cor}/r_h$)*sin($\theta_{in}-\theta_{out}$), y'=T($r_{cor}/r_{air}$)*cos($\theta_{in}-\theta_{out}$).

Figure 10:
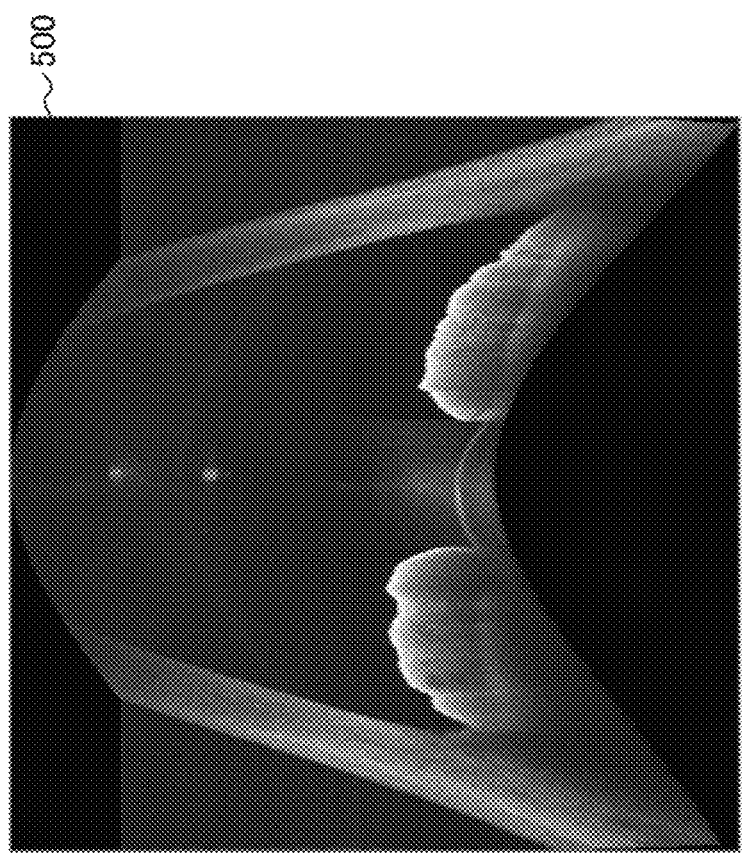
FIG. 10 is a diagram illustrating an example of processing executed by an ophthalmic apparatus according to an aspect example.

By applying such refraction correction to each point (pixel) located below the anterior corneal surface 410 in the anterior segment image 300 before distortion correction, distortion of the anterior segment image 300 caused by refraction at the anterior corneal surface can be corrected. Such distortion correction yields the anterior segment image 500 shown in FIG. 10. Note that the vertical resolutions (resolutions in the vertical direction, resolutions in the upward and downward direction of the frame) at the individual coordinates (x', y') after the refraction correction are uniformly the resolution in air "$r_{air}$".

The distortion correcting processor 232 is implemented by cooperation between hardware including one or more processors and distortion correcting software.

<Aspect Ratio Correcting Processor 233>

The aspect ratio correcting processor 233 is configured to correct the pixel aspect ratio of an anterior segment image of the subject's eye E. The image data constructing unit 220 constructs an OCT image (anterior segment image, fundus image) of a predetermined pixel aspect ratio, from data acquired by OCT scanning.

Figure 11:
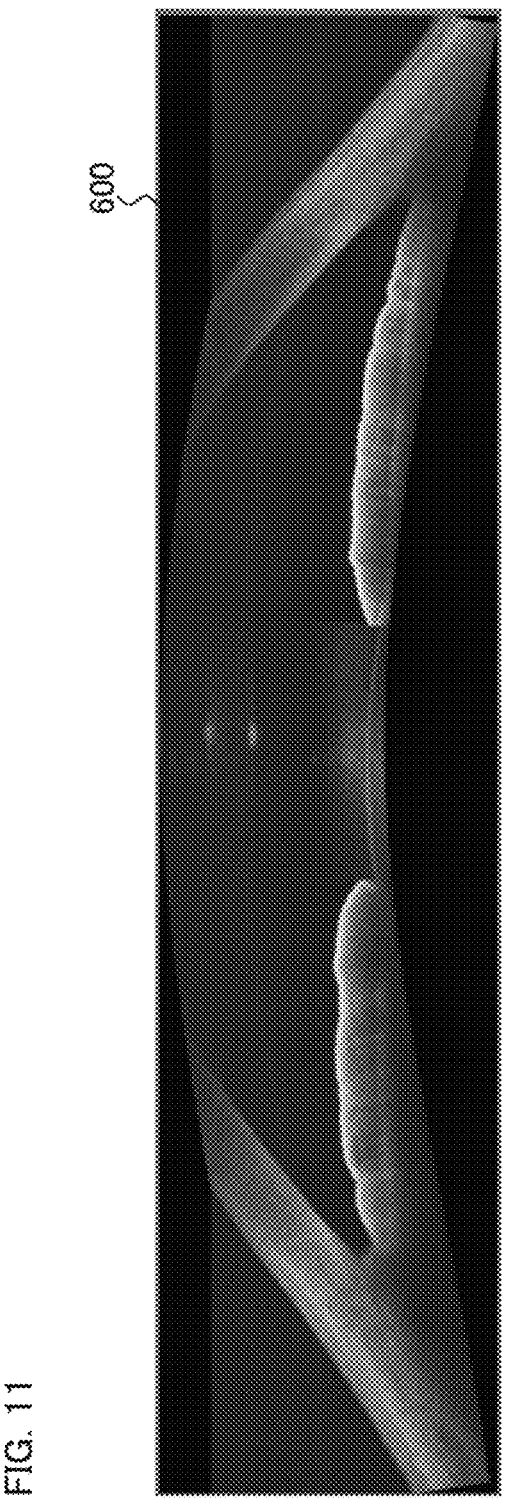
FIG. 11 is a diagram illustrating an example of processing executed by an ophthalmic apparatus according to an aspect example.

The aspect ratio correcting processor 233 of some typical aspect examples is configured to convert (transform) this OCT image into an image of the pixel aspect ratio corresponding to the real space, that is, an image of the pixel aspect ratio 1:1. This pixel aspect ratio correction yields the anterior segment image 600 shown in FIG. 11.

Execution of the pixel aspect ratio correction allows an anterior segment image that represents the actual morphology of an anterior segment to be obtained. In addition, analysis of this anterior segment image can generate analysis data that reflects the real states (real conditions) of the anterior segment such as the real scale and the real size of the anterior segment. Here, the analysis data includes, for example, one or more anterior segment parameters such as one or more corner angle parameters.

The aspect ratio correcting processor 233 of the present example is configured to correct the pixel aspect ratio of the anterior segment image whose distortion has already been corrected by the distortion correcting processor 232. In other words, the aspect ratio correcting processor 233 of the present example is configured to perform pixel aspect ratio correction after image distortion correction. However, in aspect examples, the stage in which and the timing at which pixel aspect ratio correction is performed may be freely selected. In some aspect examples, the timing of execution of pixel aspect ratio correction may be any of the followings: a time point prior to corneal shape estimation; a time point prior to anterior corneal surface region identification; a time point between anterior corneal surface region identification and curve fitting; a time point after curve fitting; a time point after corneal shape estimation; a time point prior to image distortion correction; and a time point after image distortion correction. Some aspect examples may be configured to apply correction processing equivalent to pixel aspect ratio correction, to analysis data derived by the analyzing processor 234.

The aspect ratio correcting processor 233 is implemented by cooperation between hardware including one or more processors and pixel aspect ratio correcting software.

<Analyzing Processor 234>

The analyzing processor 234 is configured to perform calculation of a predetermined anterior segment parameter by analyzing an anterior segment image of the subject's eye E.

The analyzing processor 234 of some aspect examples may be configured to perform calculation of a predetermined anterior segment parameter by analyzing an anterior segment image to which at least distortion correction has already been applied. With this configuration, it becomes possible to execute anterior segment parameter calculation with a high degree of accuracy and a high degree of precision based on an anterior segment image with distortion corrected.

Further, the analyzing processor 234 of some aspect examples may be configured to perform calculation of a predetermined anterior segment parameter by analyzing an anterior segment image to which both distortion correction and pixel aspect ratio correction have already been applied. With this configuration, it becomes possible to execute anterior segment parameter calculation with even higher degree of accuracy and even higher degree of precision based on an anterior segment image with distortion and pixel aspect ratio both corrected. Note that in the present example, pixel aspect ratio correction is performed after image distortion correction and anterior segment analysis is performed after the pixel aspect ratio correction.

The anterior segment parameter(s) calculated by the analyzing processor 234 may be freely selected. An anterior segment parameter is a value representing the morphology (shape, form) of an anterior segment. Examples of anterior eye parameters include, in addition to corner angle parameters described later, radius of curvature of anterior corneal surface, radius of curvature of posterior corneal surface, radius of curvature of anterior surface of crystalline lens, radius of curvature of posterior surface of crystalline lens, corneal diameter (vertical diameter, horizontal diameter (white-to-white)), corneal thickness (central thickness, peripheral thickness), crystalline lens thickness, anterior chamber depth, anterior chamber volume, pupil diameter, and pupil center (eccentricity). The anterior segment parameter(s) calculated by the analyzing processor 234 may include shape distribution data, and may include, for example, corneal shape maps of various kinds such as a curvature map in the axial direction (axial curvature map), a tangential curvature map, an elevation map, a refractive power map, a thickness map (pachymetry map), a wavefront aberration map.

The methods and techniques of anterior segment parameter calculation may be freely selected (see, for example, PATENT DOCUMENTS 1 to 5). In some typical examples, anterior segment parameter calculation may include a process of identifying a predetermined site of an anterior segment (e.g., a process of segmentation, a process of feature point detection), and a measurement process such as any of distance measurement, area measurement, volume measurement, ratio calculation, and angle calculation.

The analyzing processor 234 is implemented by cooperation between hardware including one or more processors and analyzing software.

<Corner Angle Analyzing Processor 2341>

The analyzing processor 234 of the present example includes the corner angle analyzing processor 2341. The corner angle analyzing processor 2341 is configured to perform calculation of a predetermined corner angle parameter by analyzing an anterior segment image. The corner angle analyzing processor 2341 of the present example is configured to perform calculation of a predetermined corner angle parameter by analyzing an anterior segment image whose distortion has been corrected by the distortion correcting processor 232 and whose pixel aspect ratio has been corrected by the aspect ratio correcting processor 233.

A corner angle parameter is a parameter related to the site called corner angle (also referred to as angle of anterior chamber or anterior chamber angle) located between cornea and iris. Trabecular meshwork exists in corner angle. The magnitude of corner angle is considered to be one of determining factors of the flow speed of aqueous humor drained from an eyeball, and therefore one of determining factors of intraocular pressure. A corner angle parameter is used as an important index (important indicator, important information) for diagnosis of glaucoma, especially diagnosis of angle closure glaucoma.

Examples of corner angle parameters include angle opening distance (AOD), anterior chamber angle (ACA), trabecular iris space area (TISA), angle recess area (ARA), and angle-to-angle distance (AtA) (see, for example, PATENT DOCUMENTS 1 to 3).

The methods and techniques of corner angle parameter calculation may be freely selected (see, for example, PATENT DOCUMENTS 1 to 3). In some typical examples, corner angle parameter calculation may include a process of identifying the position of corner angle or a predetermined position (location) in the vicinity of corner angle (e.g., a process of segmentation, a process of feature point detection), and a measurement process such as any of distance measurement, ratio calculation, and angle calculation.

The corner angle analyzing processor 2341 is implemented by cooperation between hardware including one or more processors and corner angle analyzing software.

<User Interface 240>

The user interface 240 includes the display device 241 and the operation device 242. The display device 241 includes the display device 3. The operation device 242 includes various operation devices and various input devices. The user interface 240 may include a device that has both a display function and an operation function, such as a touch panel. Some embodiment may not include at least part of the user interface 240. For example, a display device may be an external device or a peripheral device that is connected to the ophthalmic apparatus 1.

<Operation of Ophthalmic Apparatus>

Figure 12:
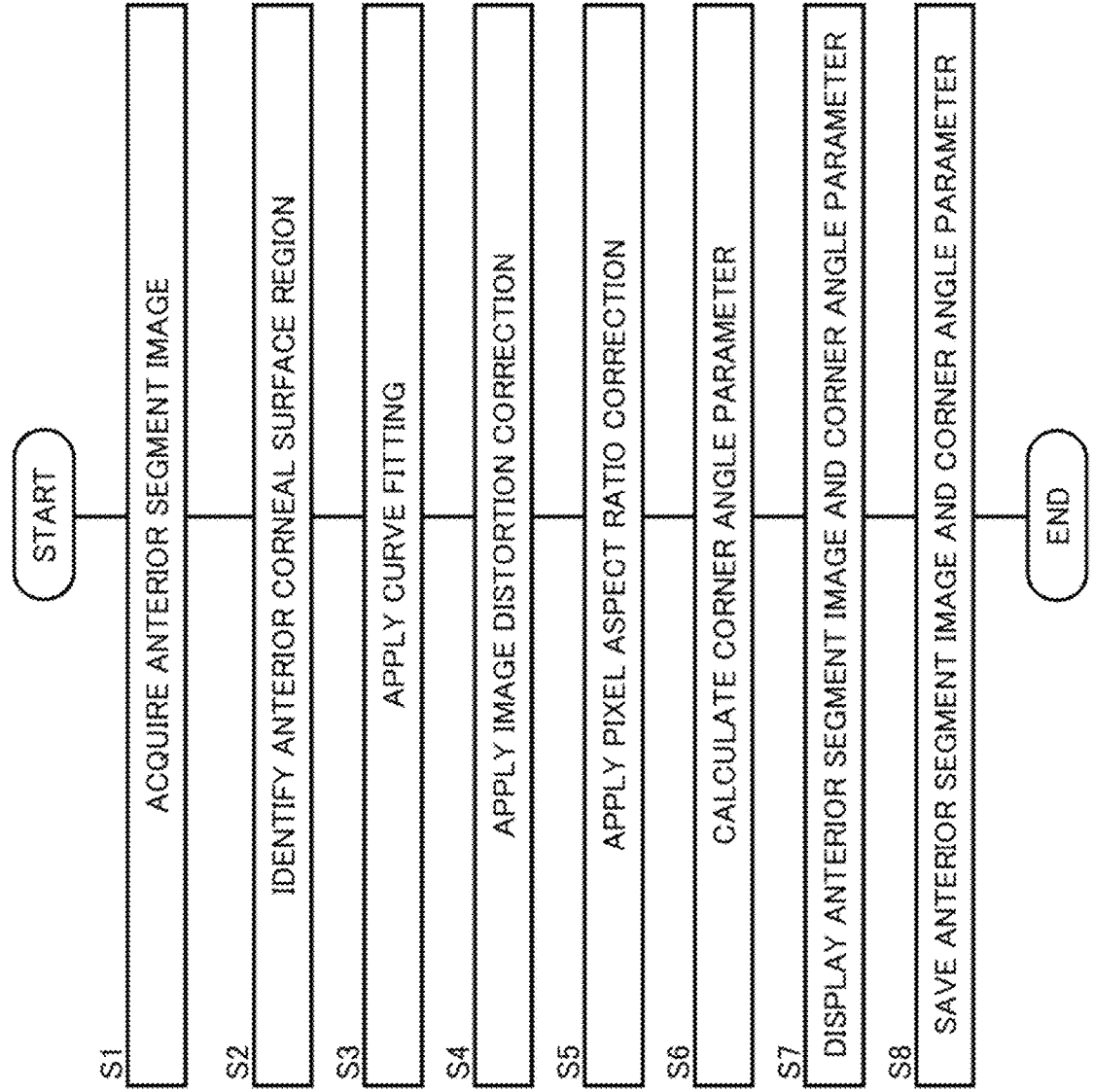
FIG. 12 is a flowchart illustrating an example of an operation executed by an ophthalmic apparatus according to an aspect example.

Several examples of the operation of the ophthalmic apparatus 1 will be described. The same or similar preparatory processes as those performed by existing or conventional ophthalmic apparatuses are performed before the operation described below. Examples of such preparatory processes may include a process of entering a patient identifier (ID), a process of inserting the anterior segment OCT attachment 400 into the sample arm, a process of presenting a fixation target to the subject's eye E, a process of adjusting fixation position, a process of alignment, a process of focus adjustment, and a process of OCT optical path length adjustment. FIG. 12 shows an example of the operation of the ophthalmic apparatus 1.

(S1: Acquire Anterior Segment Image)

First, the ophthalmic apparatus 1 acquires an anterior segment image of the subject's eye E. In the present example, the ophthalmic apparatus 1 collects data from the anterior segment Ea by applying OCT scanning to the anterior segment Ea using the OCT scanner (the sample arm in the fundus camera unit 2, and the OCT unit 100, etc.), and constructs an anterior segment image from the collected data using the image data constructing unit 220. In this way, the present example obtains the anterior segment image 300 shown in FIG. 6. The controller 210 sends the acquired anterior segment image 300 to the data processor 230. The anterior segment image 300 sent to the data processor 230 is input to the corneal shape estimating processor 231.

(S2: Identify Anterior Corneal Surface Region)

The anterior corneal surface region identifying processor 2311 of the corneal shape estimating processor 231 analyzes the anterior segment image 300 acquired in the step S1 to identify an anterior corneal surface region corresponding to the anterior surface of the cornea. In this way, the present example identifies the anterior corneal surface regions 301 and 302 shown in FIG. 6.

(S3: Apply Curve Fitting)

Next, the curve fitting processor 2312 applies curve fitting to the anterior corneal surface regions 301 and 302 identified in the step S2, to derive an approximate curve of the anterior surface of the cornea including a missing part (this missing part is a part of the cornea that is not depicted in the anterior segment image 300). In this way, the present example obtains the approximate curve 410 shown in FIG. 8.

(S4: Apply Image Distortion Correction)

Next, the distortion correcting processor 232 corrects distortion of the anterior segment image 300 based at least on the approximate curve 410 derived in the step S3. In this way, the present example obtains the anterior segment image 500 shown in FIG. 10.

(S5: Apply Pixel Aspect Ratio Correction)

Next, the aspect ratio correcting processor 233 corrects the pixel aspect ratio of the anterior segment image 500 with distortion corrected in the step S4. In this way, the present example obtains the anterior segment image 600 shown in FIG. 11.

(S6: Calculate Corner Angle Parameter)

Next, the corner angle analyzing processor 2341 of the analyzing processor 234 performs calculation of a predetermined corner angle parameter(s) by analyzing the anterior segment image 600 obtained in the step S5.

(S7: Display Anterior Segment Image and Corner Angle Parameter)

The main controller 211 displays, for example, the anterior segment image 600 obtained in the step S5 and information on the corner angle parameter(s) obtained in the step S6, on the display device 241.

Figure 13A:
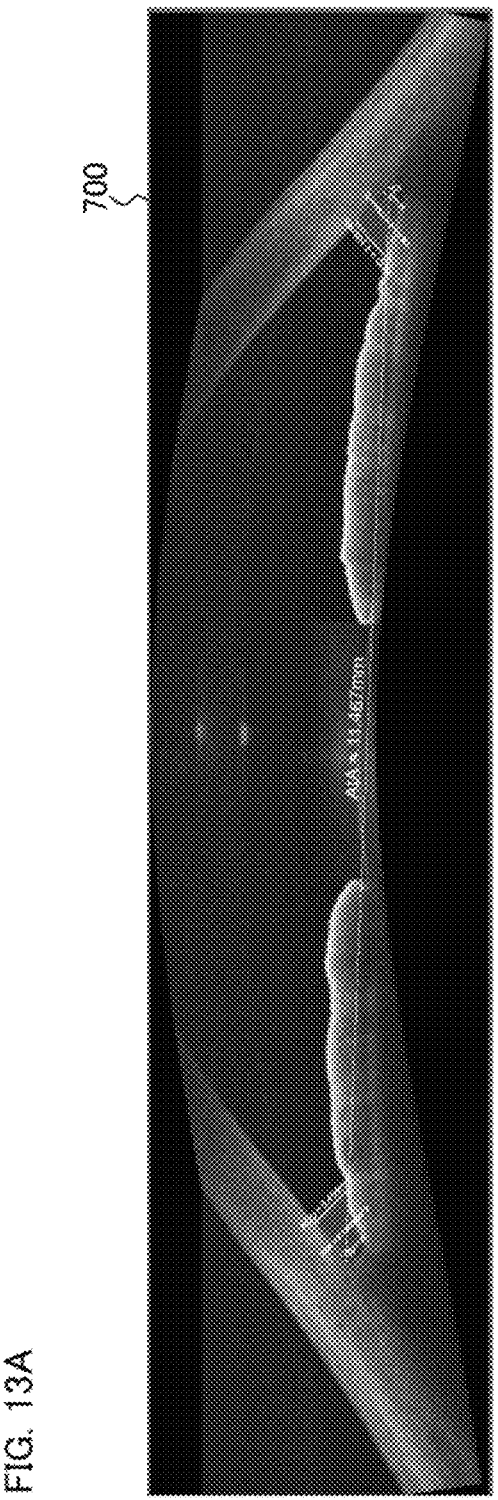
FIG. 13A is a diagram illustrating an example of an operation executed by an ophthalmic apparatus according to an aspect example.
Figure 13B:
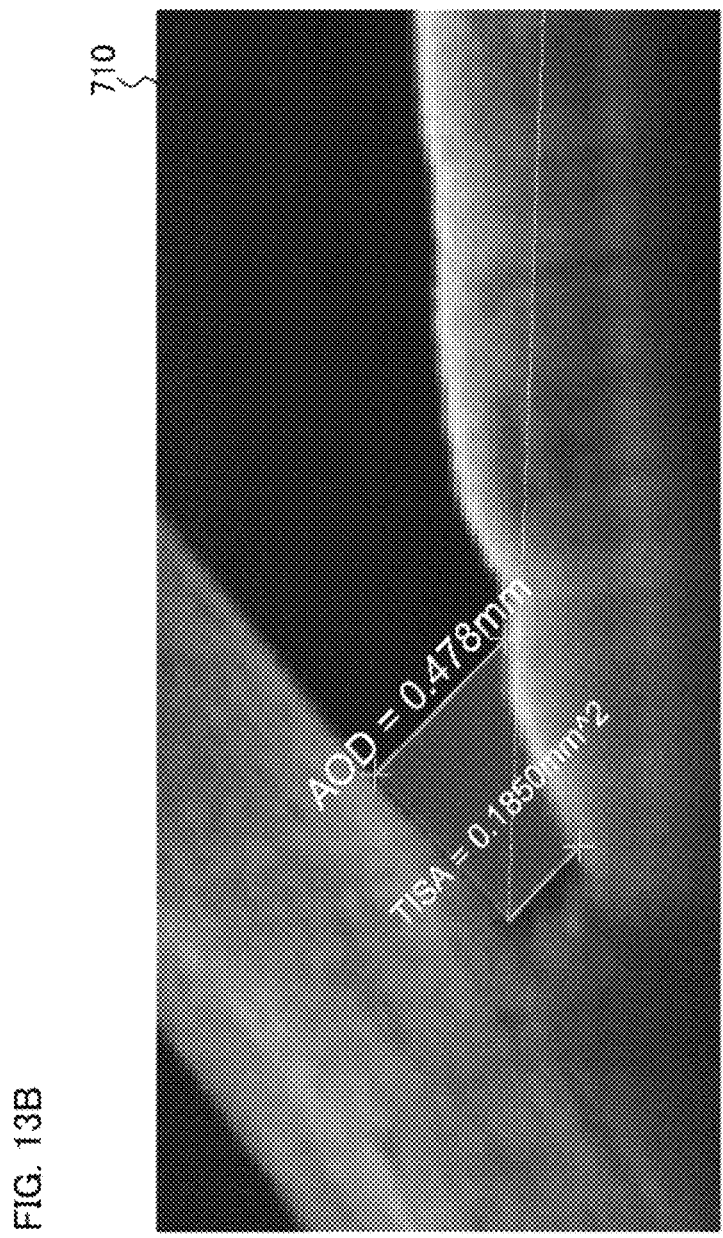
FIG. 13B is a diagram illustrating an example of an operation executed by an ophthalmic apparatus according to an aspect example.

Several examples of the information displayed in the step S7 are shown in FIG. 13A and FIG. 13B. The displayed information 700 shown in FIG. 13A presents, on the anterior segment image 600, the measurement positions and the measured values of the corner angle parameters (AOD, TISA, and AtA) obtained in the step S6. The displayed information 710 shown in FIG. 13B shows an enlarged representation of a part of the displayed information 700 shown in FIG. 13A. The displayed information 710 presents the measurement positions and the measured values of the corner angle parameters (AOD and TISA) obtained in the step S6, on the enlarged image of the corner angle and its vicinity in the anterior segment image 600.

(S8: Save Anterior Segment Image and Corner Angle Parameter)

The main controller 211 stores one or more anterior segment images of the subject's eye E and the information on the corner angle parameter obtained in the step S6 in, for example, the memory 212 and/or a storage device. The one or more anterior segment images stored may include, for example, any of the anterior segment image obtained in the step S1, the anterior segment image with distortion corrected in the step S4, and the anterior segment image with pixel aspect ratio corrected in the step S5. This completes the present operation example (End).

Modification Examples

Figure 14:
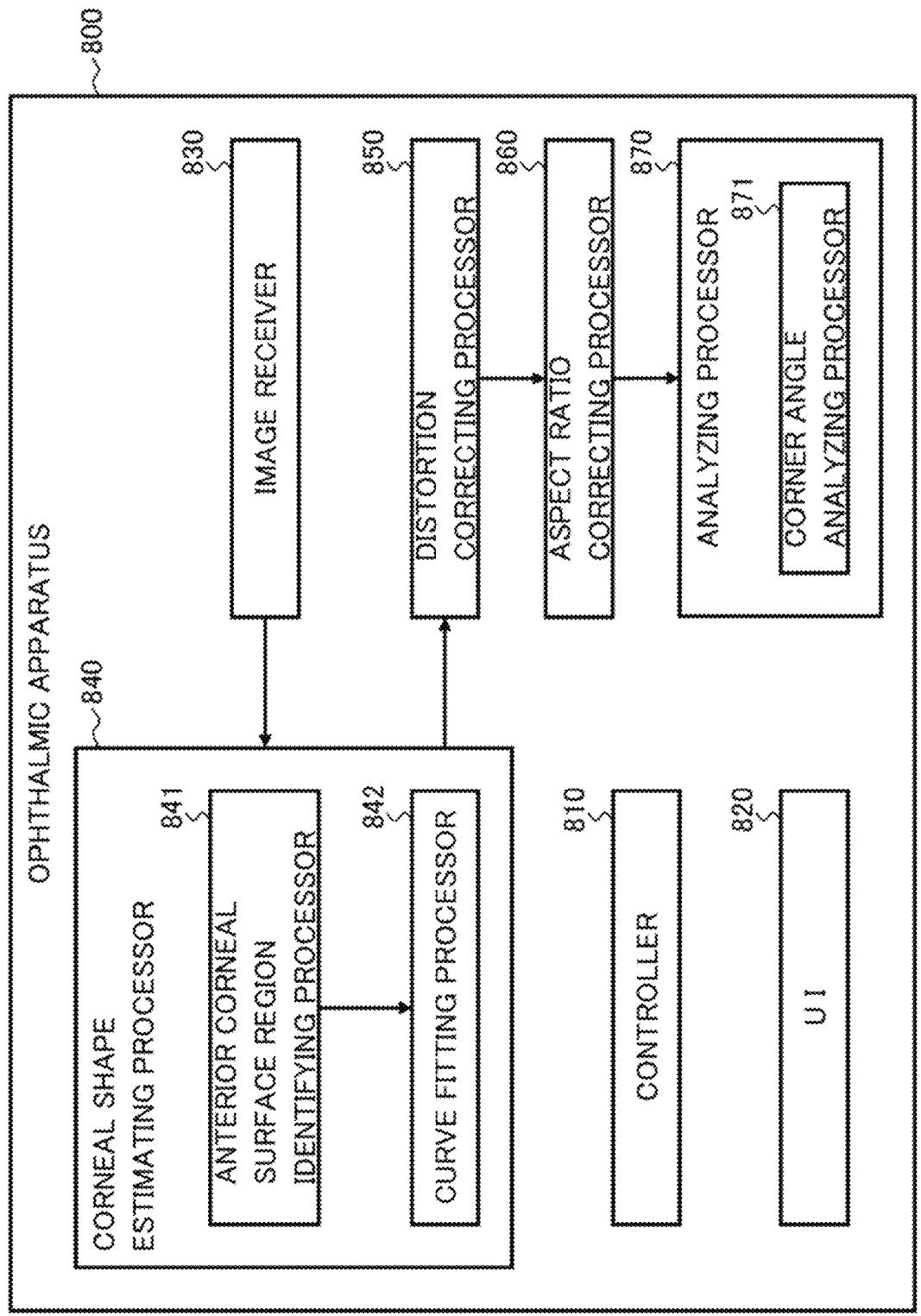
FIG. 14 is a diagram of an example of a configuration of an ophthalmic apparatus according to an aspect example.

While the ophthalmic apparatus 1 described above includes the OCT scanner and the image data constructing unit, an ophthalmic apparatus of some aspect examples may not include any one or both of an OCT scanner and an image data constructing unit. For example, the ophthalmic apparatus 800 shown in FIG. 14 includes neither an OCT scanner nor an image data constructing unit, but includes the image receiver 830 in place of the OCT scanner and the image data constructing unit.

The image receiver 830 has the function of receiving an anterior segment image of a subject's eye from an external source. In some aspect examples, the image receiver 830 may include a communication device for performing data communication with external apparatuses, and may be configured to obtain an anterior segment image of a subject's eye from an external apparatus. In some aspect examples, the image receiver 830 may include a drive device for reading out data stored in a recording medium, and may be configured to obtain an anterior segment image of a subject's eye from a recording medium.

Thus, while the ophthalmic apparatus 1 described above constructs an OCT image by itself, the ophthalmic apparatus 800 of the present modification example obtains an OCT image from an external source. The ophthalmic apparatus 800 of the present modification example may include, for example, a single computer or two or more computers, and may typically include a personal computer or a server.

Similar to the ophthalmic apparatus 1 described above, the ophthalmic apparatus 800 includes the controller 810, the user interface 820, the corneal shape estimating processor 840, the distortion correcting processor 850, the aspect ratio correcting processor 860, and the analyzing processor 870. The corneal shape estimating processor 840 includes the anterior corneal surface region identifying processor 841 and the curve fitting processor 842. The analyzing processor 870 includes the corner angle analyzing processor 871. Each of these elements may have the same (or similar) configuration and the same (or similar) function as (or to) a corresponding element in the ophthalmic apparatus 1 described above (see, for example, FIG. 5).

An example of the operation of the ophthalmic apparatus 800 will now be described with referring again to FIG. 12. First, the ophthalmic apparatus 800 acquires an anterior segment image of the subject's eye E by the image receiver 830 (S1). Note that an image corresponding to a part of the cornea is not depicted in this anterior segment image. Next, the anterior corneal surface region identifying processor 841 of the corneal shape estimating processor 840 analyzes the anterior segment image acquired in the step S1 to identify an anterior corneal surface region corresponding to the anterior surface of the cornea (S2). Next, the curve fitting processor 842 applies curve fitting to the anterior corneal surface region identified in the step S2 to derive an approximate curve of the anterior surface of the cornea including a missing part (S3). Next, the distortion correcting processor 850 performs distortion correction on the anterior segment image based at least on the approximate curve obtained in the step S3 (S4). Next, the aspect ratio correcting processor 860 performs pixel aspect ratio correction on the anterior segment image with distortion corrected in the step S4 (S5). Next, the corner angle analyzing processor 871 of the analyzing processor 870 performs calculation of a predetermined corner angle parameter by analyzing the anterior segment image obtained in the step S5 (S6). Next, the controller 810 controls the user interface 820 to display, for example, the anterior segment image obtained in the step S5 and information on the corner angle parameter obtained in the step S6 (S7). Next, the controller 810 stores, in a predetermined storage device, an anterior segment image of the subject's eye E and the information on the corner angle parameter obtained in the step S6 (S8). This completes the present operation example (End).

<Actions and Effects>

Some features, some actions, and some advantageous effects of some aspect examples of embodiments will now be described.

An ophthalmic apparatus (1; 800) according to some aspect examples includes an image acquiring unit (2, 100, 220; 830), a corneal shape estimating processor (231; 840), and a first image correcting processor (232; 850). The image acquiring unit is configured to acquire an anterior segment image (300) constructed based on data collected from an anterior segment (Ea) of a subject's eye (E) by OCT scanning. Here, the anterior segment image includes a missing part corresponding to a part of a cornea of the anterior segment. The corneal shape estimating processor is configured to perform estimation of a shape of the missing part of a cornea image by analyzing the anterior segment image acquired by the image acquiring unit. The first image correcting processor is configured to perform correction of distortion of the anterior segment image based at least on the shape of the missing part obtained by the estimation performed by the corneal shape estimating processor.

In some aspect examples, the corneal shape estimating processor (231; 840) may include an anterior corneal surface region identifying processor (2311; 841) configured to perform identification of an anterior corneal surface region corresponding to an anterior surface of the cornea by analyzing the anterior segment image. In addition, the corneal shape estimating processor may be configured to perform estimation of the shape of the missing part of the cornea image based at least on the anterior corneal surface region obtained by the identification performed by the anterior corneal surface region identifying processor.

In some aspect examples, the corneal shape estimating processor (231; 840) may further include a curve fitting processor (2312; 842) configured to apply curve fitting to the anterior corneal surface region obtained by the identification performed by the anterior corneal surface region identifying processor (2311; 841), thereby deriving an approximate curve of the anterior corneal surface region of the cornea image including the missing part.

In some aspect examples, the curve fitting processor (2312; 842) may further be configured to apply, to the anterior corneal surface region, curve fitting on the basis of a robust estimation algorithm designed for removing an outlier. This robust estimation algorithm may include a random sample consensus (RANSAC) algorithm.

In some aspect examples, the first image correcting processor (232; 850) may further be configured to perform correction of the distortion of the anterior segment image based at least on the approximate curve derived by the curve fitting processor.

In some aspect examples, the anterior corneal surface region identifying processor (2311; 841) may further be configured to perform identification of the anterior corneal surface region by applying edge detection to the anterior segment image.

In some aspect examples, the anterior corneal surface region identifying processor (2311; 841) may further be configured to perform the identification of the anterior corneal surface region by performing identification of an edge where a gradient direction is toward a frame edge of the anterior segment image and where a gradient value is equal to or greater than a predetermined threshold value.

An ophthalmic apparatus (1; 800) according to some aspect examples may further include a second image correcting processor (233; 860) configured to perform correction of a pixel aspect ratio of the anterior segment image.

In some aspect examples, the second image correcting processor (233; 860) may further be configured to perform correction of the pixel aspect ratio of the anterior segment image whose distortion has been corrected by the first image correcting processor (232; 850).

An ophthalmic apparatus (1; 800) according to some aspect examples may further include an analyzing processor (234; 870) configured to perform calculation of a predetermined anterior segment parameter by analyzing the anterior segment image whose distortion has been corrected by the first image correcting processor (232; 850) and whose pixel aspect ratio has been corrected by the second image correcting processor (233; 860).

In some aspect examples, the analyzing processor (234; 870) may include a corner angle analyzing processor (2341; 871) configured to perform calculation of a predetermined corner angle parameter by analyzing the anterior segment image whose distortion has been corrected by the first image correcting processor (232; 850) and whose pixel aspect ratio has been corrected by the second image correcting processor (233; 860).

In some aspect examples, the image acquiring unit may include a data collector (2, 100) and an image constructing processor (220). The data collector is configured to perform collection (acquisition) of data by applying OCT scanning to the anterior segment (Ea). The image constructing processor is configured to perform construction of the anterior segment image based on the data collected by the data collector.

In some aspect examples, the image acquiring unit may include a receiver (830) that receives the anterior segment image from outside (from an external source, an external device, an external apparatus, an external system, or the like).

Some aspect examples provide a method of controlling an ophthalmic apparatus. The ophthalmic apparatus to which this control method is applied includes at least a processor. This control method includes the first control step, the second control step, and the third control step.

The first control step is configured to cause the processor to execute acquisition of an anterior segment image constructed based on data collected from an anterior segment of a subject's eye by OCT scanning. Here, this anterior segment image includes a missing part corresponding to a part of a cornea.

The second control step is configured to cause the processor to execute estimation of a shape of the missing part of a cornea image by performing analysis of the anterior segment image.

The third control step is configured to cause the processor to perform correction of distortion of the anterior segment image based at least on the shape of the missing part.

Any matters and items of the aspect examples described above may be incorporated with this method of controlling an ophthalmic apparatus.

Some aspect examples provide a program configured to cause a computer (ophthalmic apparatus) to execute the method of controlling an ophthalmic apparatus. Any matters and items of the aspect examples described above may be incorporated with this program.

Some aspect examples provide a computer-readable non-transitory recording medium that retains this program. Any matters and items of the aspect examples described above may be incorporated with this recording medium. This recording medium may be in any form. Examples of this recording medium include a magnetic disk, an optical disk, a magneto-optical disk, a semiconductor memory, and any other kinds of recording media.

According to the control method, the program, or the recording medium of some aspect examples, it becomes possible to perform refraction correction even when a part of a cornea is not imaged (not depicted) in an anterior segment image by executing estimation of the shape of this missing part (the part not depicted in the anterior segment image) based on a part(s) of the cornea depicted in the anterior segment image. This allows, for example, anterior analysis such as corner angle analysis to be performed with a high degree of accuracy and/or a high degree of precision. Further, the control method, the program, or the recording medium of some aspect examples can provide additional actions and/or additional advantageous effects corresponding to matters and items optionally incorporated.

According to the aspect examples described in the present disclosure, it becomes possible to perform refraction correction even when a part of a cornea is not imaged (not depicted) in an anterior segment image by executing estimation of the shape of this missing part (the part not depicted in the anterior segment image) based on a part(s) of the cornea depicted in the anterior segment image. This allows, for example, anterior analysis such as corner angle analysis to be performed with a high degree of accuracy and/or a high degree of precision.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus comprising:
an image acquiring circuit configured to acquire an anterior segment image constructed based on data collected from an anterior segment of a subject's eye by optical coherence tomography (OCT) scanning, the anterior segment image including a missing part corresponding to a part of a cornea;
a corneal shape estimating processor circuit configured to estimate a shape of the missing part of a cornea image by analyzing the anterior segment image acquired by the image acquiring circuit;
a first image correcting processor circuit configured to correct distortion of the anterior segment image based at least on the shape of the missing part estimated by the corneal shape estimating processor circuit; and
a second image correcting processor circuit configured to correct a pixel aspect ratio of the anterior segment image,
wherein the second image correcting processor circuit is further configured to perform correction of the pixel aspect ratio of the anterior segment image whose distortion has been corrected by the first image correcting processor circuit.

2. The ophthalmic apparatus of claim 1, wherein
the corneal shape estimating processor circuit includes an anterior corneal surface region identifying processor circuit configured to identify an anterior corneal surface region corresponding to an anterior surface of the cornea by analyzing the anterior segment image, and
the corneal shape estimating processor circuit is further configured to perform estimation of the shape of the missing part based at least on the anterior corneal surface region identified by the anterior corneal surface region identifying processor circuit.

3. The ophthalmic apparatus of claim 2, wherein the corneal shape estimating processor circuit further includes a curve fitting processor circuit configured to apply curve fitting to the anterior corneal surface region identified by the anterior corneal surface region identifying processor circuit to derive an approximate curve of the anterior corneal surface region of the cornea image including the missing part.

4. The ophthalmic apparatus of claim 3, wherein the curve fitting processor circuit is further configured to apply, to the anterior corneal surface region, curve fitting based on a robust estimation algorithm for removing an outlier.

5. The ophthalmic apparatus of claim 4, wherein the robust estimation algorithm includes a random sample consensus (RANSAC) algorithm.

6. The ophthalmic apparatus of claim 3, wherein the first image correcting processor circuit is further configured to perform correction of the distortion of the anterior segment image based at least on the approximate curve.

7. The ophthalmic apparatus of claim 2, wherein the anterior corneal surface region identifying processor circuit is further configured to perform identification of the anterior corneal surface region by applying edge detection to the anterior segment image.

8. The ophthalmic apparatus of claim 7, wherein the anterior corneal surface region identifying processor circuit is further configured to perform the identification of the anterior corneal surface region by identifying an edge where a gradient direction is toward a frame edge of the anterior segment image and where a gradient value is equal to or greater than a predetermined threshold value.

9. The ophthalmic apparatus of claim 1, further comprising an analyzing processor circuit configured to perform calculation of a predetermined anterior segment parameter by analyzing the anterior segment image whose distortion has been corrected by the first image correcting processor circuit and whose pixel aspect ratio has been corrected by the second image correcting processor circuit.

10. The ophthalmic apparatus of claim 9, wherein the analyzing processor circuit includes a corner angle analyzing processor circuit configured to perform calculation of a predetermined corner angle parameter by analyzing the anterior segment image whose distortion has been corrected by the first image correcting processor circuit and whose pixel aspect ratio has been corrected by the second image correcting processor circuit.

11. The ophthalmic apparatus of claim 1, wherein the image acquiring circuit includes:
 a data collector circuit configured to collect data by applying OCT scanning to the anterior segment; and
 an image constructing processor circuit configured to construct the anterior segment image based on the data collected by the data collector circuit.

12. The ophthalmic apparatus of claim 1, wherein the image acquiring circuit includes a receiver circuit that receives the anterior segment image from outside.

13. A method of controlling an ophthalmic apparatus that includes a processor, the method comprising:
 causing the processor to acquire an anterior segment image constructed based on data collected from an anterior segment of a subject's eye by optical coherence tomography (OCT) scanning, the anterior segment image including a missing part corresponding to a part of a cornea;
 causing the processor to estimate a shape of the missing part of a cornea image by analyzing the anterior segment image;
 causing the processor to correct distortion of the anterior segment image based at least on the shape of the missing part;
 correcting a pixel aspect ratio of the anterior segment image; and
 correcting the pixel aspect ratio of the anterior segment image whose distortion has been corrected by the processor.

14. A computer-readable non-transitory recording medium storing a program that causes a computer to execute the method of claim 13.

* * * * *